US012747226B2

(12) United States Patent
Waetzig et al.

(10) Patent No.: US 12,747,226 B2
(45) Date of Patent: Sep. 29, 2026

(54) METHOD OF PREPARING PRALSETINIB

(71) Applicant: Rigel Pharmaceuticals, Inc., South San Francisco, CA (US)

(72) Inventors: Joshua Waetzig, Cambridge, MA (US); Gordon D. Wilkie, Cambridge, MA (US); Vincent Poral, Groningen (NL); Albert Cornelis Dros, Groningen (NL)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 539 days.

(21) Appl. No.: 18/255,402

(22) PCT Filed: Dec. 3, 2021

(86) PCT No.: PCT/US2021/061754

§ 371 (c)(1),
(2) Date: Jun. 1, 2023

(87) PCT Pub. No.: WO2022/120136

PCT Pub. Date: Jun. 9, 2022

(65) Prior Publication Data

US 2024/0059672 A1 Feb. 22, 2024

Related U.S. Application Data

(60) Provisional application No. 63/121,330, filed on Dec. 4, 2020.

(51) Int. Cl.
*C07D 401/14* (2006.01)

(52) U.S. Cl.
CPC ........ *C07D 401/14* (2013.01); *C07B 2200/09* (2013.01)

(58) Field of Classification Search
CPC .......................... C07D 401/14; C07B 2200/09
See application file for complete search history.

(56) References Cited

U.S. PATENT DOCUMENTS

| | | | |
|---|---|---|---|
| 8,088,806 | B2 | 1/2012 | Zhang et al. |
| 8,802,697 | B2 | 8/2014 | Bifulco, Jr. |
| 9,126,951 | B2 | 9/2015 | Bifulco, Jr. |
| 9,187,475 | B2 | 11/2015 | Kawamura et al. |
| 9,200,002 | B2 | 12/2015 | Hodous et al. |
| 9,216,172 | B2 | 12/2015 | Kohno et al. |
| 9,297,011 | B2 | 3/2016 | Downing et al. |
| 9,334,263 | B2 | 5/2016 | Hodous et al. |
| 9,340,514 | B2 | 5/2016 | Bifulco, Jr. |
| 9,434,700 | B2 | 9/2016 | Bifulco, Jr. |
| 9,499,522 | B2 | 11/2016 | DiPietro et al. |
| 9,688,680 | B2 | 6/2017 | Hodous |
| 9,695,165 | B2 | 7/2017 | Bifulco, Jr. |
| 9,884,861 | B2 | 2/2018 | Hodous et al. |
| 9,944,651 | B2 | 4/2018 | Hodous et al. |
| 9,994,552 | B2 | 6/2018 | DiPietro et al. |
| 9,994,575 | B2 | 6/2018 | Hodous et al. |
| 10,000,490 | B2 | 6/2018 | Bifulco, Jr. |
| 10,000,496 | B2 | 6/2018 | Hodous et al. |
| 10,017,512 | B2 | 7/2018 | Wenglowsky et al. |
| 10,030,005 | B2 | 7/2018 | Brubaker et al. |
| 10,035,789 | B2 | 7/2018 | Brubaker et al. |
| 10,183,928 | B2 | 1/2019 | Kim et al. |
| 10,196,436 | B2 | 2/2019 | Miduturu |
| 10,202,365 | B2 | 2/2019 | Brooijmans et al. |
| 10,221,154 | B2 | 3/2019 | Bifulco, Jr. et al. |
| 10,227,329 | B2 | 3/2019 | Brubaker et al. |
| 10,584,114 | B2 | 3/2020 | Brubaker et al. |
| 10,774,070 | B2 | 9/2020 | Brooijmans et al. |
| 11,273,160 | B2 | 3/2022 | Evans Raab et al. |
| 11,279,688 | B2 | 3/2022 | Brubaker et al. |
| 11,872,192 | B2 | 1/2024 | Evans Raab et al. |
| 11,963,958 | B2 | 4/2024 | Evans Raab et al. |
| 2012/0316137 | A1 | 12/2012 | Huang et al. |
| 2013/0096136 | A1 | 4/2013 | Hata et al. |
| 2013/0115313 | A1 | 5/2013 | Charrier et al. |
| 2013/0116280 | A1 | 5/2013 | Ju et al. |
| 2014/0187559 | A1 | 7/2014 | Miduturu |
| 2014/0221404 | A1 | 8/2014 | Kohno et al. |
| 2014/0243357 | A1 | 8/2014 | Dar et al. |
| 2014/0272951 | A1 | 9/2014 | Chakravarti et al. |
| 2015/0057335 | A1 | 2/2015 | Kohno et al. |
| 2015/0177246 | A1 | 6/2015 | Shibata et al. |
| 2016/0102097 | A1 | 4/2016 | Hodous et al. |
| 2017/0014413 | A1 | 1/2017 | Downing et al. |
| 2017/0022206 | A1 | 1/2017 | Hodous et al. |

(Continued)

FOREIGN PATENT DOCUMENTS

| | | | |
|---|---|---|---|
| CN | 104844567 | A | 8/2015 |
| CN | 105255927 | A | 1/2016 |

(Continued)

OTHER PUBLICATIONS

Abdel-Rahman, O. and M. Fouad (2014) "Risk of cardiovascular toxicities in patients with solid tumors treated with sunitinib, axitinib, cediranib or regorafenib: an updated systematic review and comparative meta-analysis" Crit Rev Oncol Hematol,92:194-207.
Ahn M. et al. "OA 09.03 TATTON Ph lb Expansion Cohort: Osimertinib plus Savolitinib for Pts with EGFR-Mutant MET-Amplified NSCLC after Progression on Prior EGFR-TKI." J Thorac Oncol. 12(11) S1768, 2017.
Anonymous "BLU-667 Targets RET-Altered Cancers" Cancer Discovery, vol. 8, No. 6, OF8, Jun. 2018 (Jun. 2018), p. 5pp, XP002792436, Retrieved from the Internet: URL:http://cancerdiscovery.aacrjournals.or g/content/8/6/OF8.long [retrieved on Jun. 25, 2019].
Anonymous "Estimating the Maximum Safe Starting Dose in Initial Clinical Trials for Therapeutics in Adult Healthy Volunteers", Guidance for Industry, Jul. 1, 2005 (Jul. 1, 2005), pp. 1-30, XP093000005, Retrieved from the Internet: URL:https://www.fda.gov/media/ 72309/download [retrieved on Nov. 21, 2022].

(Continued)

*Primary Examiner* — Brandon J Fetterolf
(74) *Attorney, Agent, or Firm* — Jones Day

(57) ABSTRACT

Provided herein, in part, are compounds and compositions useful for preparing pralsetinib. Also provided herein are processes for preparing pralsetinib.

20 Claims, No Drawings

(56) References Cited

U.S. PATENT DOCUMENTS

| | | | |
|---|---|---|---|
| 2017/0029409 | A1 | 2/2017 | DiPietro et al. |
| 2017/0057953 | A1 | 3/2017 | Hodous et al. |
| 2017/0066773 | A1 | 3/2017 | Wenglowsky et al. |
| 2017/0066812 | A1 | 3/2017 | Bifulco, Jr. |
| 2017/0121312 | A1 | 5/2017 | Brubaker et al. |
| 2017/0145018 | A1 | 5/2017 | Wenglowsky et al. |
| 2017/0174652 | A1 | 6/2017 | Bifulco, Jr. |
| 2017/0204104 | A1 | 7/2017 | Hodous et al. |
| 2017/0253593 | A1 | 9/2017 | Bifulco, Jr. et al. |
| 2017/0267661 | A1 | 9/2017 | Kim et al. |
| 2017/0281633 | A1 | 10/2017 | Boylan et al. |
| 2017/0298069 | A1 | 10/2017 | Brooijmans et al. |
| 2018/0022731 | A1 | 1/2018 | Brooijmans et al. |
| 2018/0022732 | A1 | 1/2018 | Brubaker et al. |
| 2018/0030032 | A1 | 2/2018 | Brubaker et al. |
| 2019/0185454 | A1 | 6/2019 | Brubaker et al. |
| 2019/0192522 | A1 | 6/2019 | Hagel et al. |
| 2020/0407341 | A1 | 12/2020 | Brubaker et al. |
| 2021/0085680 | A1 | 3/2021 | Evans Raab et al. |
| 2021/0100795 | A1 | 4/2021 | Evans Raab et al. |
| 2021/0100799 | A1 | 4/2021 | Evans Raab et al. |
| 2021/0308134 | A1 | 10/2021 | Hata et al. |
| 2022/0175773 | A1 | 6/2022 | Evans Raab et al. |
| 2022/0315560 | A1 | 10/2022 | Brubaker et al. |
| 2023/0203009 | A1 | 6/2023 | Waetzig et al. |
| 2023/0295121 | A1 | 9/2023 | Waetzig et al. |

FOREIGN PATENT DOCUMENTS

| | | | |
|---|---|---|---|
| CN | 107980784 | A | 5/2018 |
| CN | 108341782 | A | 7/2018 |
| CN | 111362923 | A | 7/2020 |
| CN | 111440151 | A | 7/2020 |
| EP | 3037547 | A1 | 6/2016 |
| JP | 2015109806 | A | 6/2015 |
| WO | WO-2001/60816 | A1 | 8/2001 |
| WO | WO-2004/009087 | A1 | 1/2004 |
| WO | WO-2005/062795 | A2 | 7/2005 |
| WO | WO-2007/023382 | A2 | 3/2007 |
| WO | WO-2007/087245 | A2 | 8/2007 |
| WO | WO-2007/124221 | A1 | 11/2007 |
| WO | WO-2007/136103 | A1 | 11/2007 |
| WO | WO-2008/061201 | A1 | 5/2008 |
| WO | WO-2009/003136 | A1 | 12/2008 |
| WO | WO-2009/007748 | A2 | 1/2009 |
| WO | WO-2009/014637 | A2 | 1/2009 |
| WO | WO-2009/018415 | A1 | 2/2009 |
| WO | WO-2009/100536 | A1 | 8/2009 |
| WO | WO-2010/006432 | A1 | 1/2010 |
| WO | WO-2010/111056 | A1 | 9/2010 |
| WO | WO-2010/144359 | A1 | 12/2010 |
| WO | WO-2010/144394 | A1 | 12/2010 |
| WO | WO-2011/060295 | A1 | 5/2011 |
| WO | WO-2013/077921 | A2 | 5/2013 |
| WO | WO-2013/133367 | A1 | 9/2013 |
| WO | WO-2013/170159 | A1 | 11/2013 |
| WO | WO-2014/039971 | A1 | 3/2014 |
| WO | WO-2014/050781 | A1 | 4/2014 |
| WO | WO-2014/072220 | A1 | 5/2014 |
| WO | WO-2014/130810 | A1 | 8/2014 |
| WO | WO-2014/141187 | A1 | 9/2014 |
| WO | WO-2014/147640 | A2 | 9/2014 |
| WO | WO-2015/006875 | A1 | 1/2015 |
| WO | WO-2015/079251 | A1 | 6/2015 |
| WO | WO-2016/037578 | A1 | 3/2016 |
| WO | WO-2016/038552 | A1 | 3/2016 |
| WO | WO-2016/075224 | A1 | 5/2016 |
| WO | WO-2016/127074 | A1 | 8/2016 |
| WO | WO-2017/011776 | A1 | 1/2017 |
| WO | WO-2017/079117 | A1 | 5/2017 |
| WO | WO-2017/079121 | A2 | 5/2017 |
| WO | WO-2017/100642 | A1 | 6/2017 |
| WO | WO-2017/145050 | A1 | 8/2017 |
| WO | WO-2017/161269 | A1 | 9/2017 |
| WO | WO-2017/178844 | A1 | 10/2017 |
| WO | WO-2017/178845 | A1 | 10/2017 |
| WO | WO2017079140 | A1 * | 11/2017 |
| WO | WO-2018/017983 | A1 | 1/2018 |
| WO | WO-2018/022761 | A1 | 2/2018 |
| WO | WO-2018/049233 | A1 | 3/2018 |
| WO | WO-2018/060714 | A1 | 4/2018 |
| WO | WO-2018/064852 | A1 | 4/2018 |
| WO | WO-2018/071447 | A1 | 4/2018 |
| WO | WO-2018/071454 | A1 | 4/2018 |
| WO | WO-2018/102455 | A1 | 6/2018 |
| WO | WO-2018/136661 | A1 | 7/2018 |
| WO | WO-2018/136663 | A1 | 7/2018 |
| WO | WO-2018/183712 | A1 | 10/2018 |
| WO | WO-2018/189553 | A1 | 10/2018 |
| WO | WO-2018/213329 | A1 | 11/2018 |
| WO | WO-2018/237134 | A1 | 12/2018 |
| WO | WO-2019/001556 | A1 | 1/2019 |
| WO | WO-2019/008172 | A1 | 1/2019 |
| WO | WO-2019/126121 | A1 | 6/2019 |
| WO | WO-2019/143977 | A1 | 7/2019 |
| WO | WO-2019/143991 | A1 | 7/2019 |
| WO | WO-2019/143994 | A1 | 7/2019 |
| WO | WO-2019/195471 | A1 | 10/2019 |
| WO | WO-2020/033838 | A2 | 2/2020 |
| WO | WO-2021/243186 | A1 | 12/2021 |
| WO | WO-2021/243192 | A1 | 12/2021 |
| WO | WO-2022/120136 | A1 | 6/2022 |

OTHER PUBLICATIONS

Anonymous, “Phase 1 Study of the Highly-selective RET Inhibitor BLU-667 in Patients With Thyroid Cancer, Non-Small Cell Lung Cancer, and Other Advanced Solid Tumors,” ClinicalTrials.org Internet Citation, Apr. 21, 2017 (Apr. 21, 2017), p. 8pp, XP002783685.

Anonymous: “Phase 1 Study of the Highly-selective RET Inhibitor BLU-667 in Patients With Thyroid Cancer, Non-Small Cell Lung Cancer, and Other Advanced Solid Tumors,” Internet Citation, Apr. 21, 2017, Retrieved from the Internet: URL:https://www.clinicaltrials.gov/ct2/history/NCT03037385?V _3=View#StudyPageTop.

Antonescu, C.R. et al. (Jul. 2015) “Molecular Characterization of Inflammatory Myofibroblastic Tumors with Frequent ALK and ROS1 Fusions and Rare Novel RET Gene Rearrangement” Am J Surg Pathol, 39(7):957-967. HHS Public Access Author Manuscript; available in PMC Jul. 1, 2015 (19 pages).

Arighi, E. et al. (2005) “RET tyrosine kinase signaling in development and cancer” Cytokine & Growth Factor Reviews, 16:441-467.

Baselga, J. et al. (2005) “Phase II and Tumor Pharmacodynamic Study of Gefitinib in Patients with Advanced Breast Cancer” J Clin Oncol, 23(23):5323-5333.

Bentzien, F. et al. (2013) “In Vitro and in Vivo Activity of Cabozantinib (XL184), an Inhibitor of RET, MET, and VEGFR2, in a Model of Medullary Thyroid Cancer” Thyroid, 23(12):1569-1577.

Brandt, W. et al. (2010) “Inhibitors of the RET tyrosine kinase based on a 2-(alkylsulfanyl)-4-(3-thienyl) nicotinonitrile scaffold” Eur J Med Chem, 45:2919-2927.

Brown et al. (1984) “Heterocyclic Amplifiers of Phleomycin. IV Pyrimidinylpurines, Phenylpyrimidines and Related Systems with Basic Side Chains,” Aust. J. Chem., 37:2093-101.

Caira (1998) “Crystalline Polymorphism of Organic Compounds,” Topics in Current Chemistry 198:163-208.

Caprelsa (vandetanib) “Full Prescribing Information” Reference ID: 3964956, Cambridge, MA: Sanofi Genzyme; 2016.

Carlomagno, F et al. (Feb. 1995) “Point Mutation of the Ret Proto-oncogene in the TT Human Medullary Thyroid Carcinoma Cell Line” Biochem Biophys Res Common, 207(3):1022-1028.

Cascone, T. et al., “Significant Systemic and CNS Activity of RET Inhibitor Vandetanib Combined with mTOR Inhibitor Everolimus in Patients with Advanced NSCLC with RET Fusion”, J. of Clinical Oncology 34, No. 15, 2 pages.

Ceccherini, I. et al. (1997) “Somatic in frame deletions not involving juxtamembranous cysteine residues strongly activate the RET proto-oncogene” Oncogene, 14:2609-2612.

Chalice Software Technical Guide, Horizon CombinatoRx Inc., Cambridge, MA, USA (downloaded Jul. 2018).

(56) References Cited

OTHER PUBLICATIONS

Chen, M-H et al. (2014) "Antitumor activity of the combination of a HSP90 inhibitor and a PI3K/mTOR dual inhibitor against cholangiocarcinoma," Oncotarget, 5(8):2372-2389.
Chilean Search Report dated Jun. 27, 2022, in Chilean Patent Application No. 202002544, Chilean National Stage of International Patent Application No. PCT/US2019/025655, filed Apr. 3, 2019, by Blueprint Medicines Corp.
Chilean Search Report dated Mar. 16, 2023, in Chilean Patent Application No. 202002544, Chilean National Stage of International Patent Application No. PCT/US2019/025655, filed Apr. 3, 2019, by Blueprint Medicines Corp.
Cometriq (cabozantinib)"Full Prescribing Information" Reference ID: 3964956, South San Francisco, CA: Exelixix, Inc.; 2018.
Drilon et al. (2018) "Targeting RET-driven cancers: lessons from evolving preclinical and clinical landscapes," *Nature Reviews Clinical Oncology* 15:151-167.
Druker, B.J. et al. (2001) "Efficacy and Safety of a Specific Inhibitor of the BCR-ABL Tyrosine Kinase in Chronic Myeloid Leukemia" New Engl J Med, 344(14):1031-1037.
Eisenhauer, E.A. et al. (2009) "New response evaluation criteria in solid tumours: Revised RECIST guideline (version 1.1)" Eur J Cancer, 45:228-247.
Elisei, R. et al. (2008) "Prognostic Significance of Somatic RET Oncogene Mutations in Sporadic Medullary Thyroid Cancer: A 10-Year Follow-Up Study" J Clin Endocrinol Metab, 93(3):682-687.
Engelman J.A. et al. "MET Amplification Leads to Gefitinib Resistance in Lung Cancer by Activating ERBB3 Signaling." Science, 2007, 316 (5827), pp. 1039-1043.
Evans, E. (May 1, 2016) "The Development of Potent and Selective RET Inhibitors" Slides presented at the 2016 Annual Meeting of the International Thyroid Oncology Group at the University of Colorado (19 pages).
Fagin, J.A. et al. "Biologic and Clinical Perspectives on Thyroid Cancer." N Engl J Med. 2016, 375(11) pp. 1054-1067.
Fang, P. et al. (Feb. 2016) "Detection of a novel RET gene fusion in a non-small cell lung cancer patient using AMP chemistry" J Thorac Oncol, 11.2:S21-S22.
Ferrara et al. "Clinical and Translational Implications of RET Rearrangements in Non-Small Cell Lung Cancer," Journal of Thoracic Oncology, 2018, 13, pp. 27-45.
Gainor J.F. et al. "Dramatic Response to Combination Erlotinib and Crizotinib in a Patient with Advanced, EGFR-Mutant Lung Cancer Harboring De Novo MET Amplification." J Thorac Oncol. 11(7) 2016, pp. e83-e85.
Gautschi, O. et al. (2016) "Targeting RET in patients with RET-rearranged lung cancers: Results from a global registry" J Clin Oncol, 34(15S) (suppl; abstr 9014).
Gild, M.L. et al. (Oct. 2013) "Targeting mTOR in RET mutant medullary and differentiated thyroid cancer cells" Endocr Re/at Cancer, 20(5):659-667. HHS Public Access Author Manuscript; available in PMC Mar. 27, 2015 (16 pages).
Graham et al., 17 Bioorganic & Medicinal Chemistry, 5886-5893 (2007).
Grubbs, E.G. et al. (Mar. 2015) "RET Fusion as a Novel Driver of Medullary Thyroid Carcinoma" J Clin Endocrinol Metab, 100:788-793.
Halkova, T. et al. (2015) "A novel RET/PTC variant detected in a pediatric patient with papillary thyroid cancer without ionization history" Hum Pathol, 46:1962-1969.
Hayashi, H. et al. (2000) "Characterization of intracellular signals via tyrosine 1062 in RET activated by glial cell line-derived neurotrophic factor" Oncogene, 19:4469-4475.
Hilfiker et al. (2006) "Relevance of Solid-state Properties for Pharmaceutical Products," Polymorphism in the Pharmaceutical Industry, XP002528052, 19 pages.
Horiike, A. et al. (2016) "Sorafenib treatment for patients with RET fusion-positive non-small cell lung cancer" Lung Cancer, 93:43-46.
Hughes (2021) "Review of Synthetic Routes and Crystalline Forms of the Oncology Drugs Capmatinib, Selpercatinib, and Pralsetinib," Org. Process Res. Dev. 25:2192-2204.
International Search Report and Written Opinion dated Apr. 29, 2016, in International Patent Application No. PCT/US2016/016808, filed Feb. 5, 2016, by Blueprint Medicines Corp. (8 pages).
International Search Report and Written Opinion dated Aug. 16, 2021, in International Patent Application No. PCT/US2021/034823, filed May 28, 2021, by Blueprint Medicines Corp. (14 pages).
International Search Report and Written Opinion dated Feb. 24, 2022, in International Patent Application No. PCT/US2021/061754, filed Dec. 3, 2021, by Blueprint Medicines Corp. (16 pages.
International Search Report and Written Opinion dated Jan. 18, 2017, in International Patent Application No. PCT/US2016/059879, filed Nov. 1, 2016, by Blueprint Medicines Corp. (12 pages).
International Search Report and Written Opinion dated Jun. 12, 2017, in International Patent Application No. PCT/US2017/022969, filed Mar. 17, 2017, by Blueprint Medicines Corp. (12 pages).
International Search Report and Written Opinion dated May 11, 2021, in International Patent Application No. PCT/US2021/034811, filed May 28, 2021, by Blueprint Medicines Corp. (16 pages).
International Search Report and Written Opinion dated Oct. 12, 2017, in International Patent Application No. PCT/US2017/043964, filed Jul. 26, 2017, by Blueprint Medicines Corp. (13 pages).
International Search Report and Written Opinion dated Oct. 25, 2017, in International Patent Application No. PCT/US2017/043340, filed Jul. 21, 2017, by Blueprint Medicines Corp. (14 pages).
International Search Report and Written Opinion mailed Aug. 21, 2018, in International Patent Application No. PCT/US2018/032794, filed May 15, 2018, by Blueprint Medicines Corp. (18 pages).
International Search Report and Written Opinion of the International Searching Authority for Intenational Application No. PCT/US2019/025655 mailed Jul. 23, 2019 (16 pages).
International Search Report and Written Opinion of the International Searching Authority for International Application No. PCT/US2019/045919 mailed Jan. 22, 2020 (11 pages).
Jin, N. et al. (Oct. 15, 2011), "Synergistic Action of a RAF Inhibitor and a Dual PI3K/mTOR Inhibitor in Thyroid Cancer," Clin Cancer Res, 17(20):6482-6489.
Joung, J.Y. et al. (2016) "Diffuse sclerosing variant of papillary thyroid carcinoma: major genetic alterations and prognostic implications" Histopathology, 69:45-53.
Jovanovic, R. et al. (2015) "Novel RET Mutations in Macedonian Patients with Medullary Thyroid Carcinoma: Genotype-Phenotype Correlations" Prilozi, 36(1):93-107.
Kamil et al. "Dose estimation, conversion and translation from animal to human and human to animal for clinical and animal studies", Int. J. Biol. Biotech., Jul. 1, 2017 (Jul. 1, 2017), pp. 311-317, XP093000013, Retrieved from the Internet: URL:https://www.researchgate.net/publication/322329638_Dose_estimation_conversion_and_translation_from_animal_to_human_and_human_to_animal_for_clinical_and_animal_studies [retrieved on Nov. 21, 2022].
Kang et al., "Osimertinib and Cabozantinib Combinatorial Therapy in an EGFR-Mutant Lung Adenocarcinoma Patient with Multiple MET Secondary-Site Mutations after Resistance to Crizotinib," Journal of Thoracic Oncology, Apr. 2018, vol. 13, No. 4, pp. e49-e53.
Karrasch, T. et al. (2016) "How to Assess the Clinical Relevance of Novel RET Missense Variants in the Absence of Functional Studies?" Eur Thyroid J, 5:73-77.
Kato, S. et al. (Apr. 15, 2017) "RET Aberrations in Diverse Cancers: Next-Generation Sequencing of 4,871 Patients" Clin Cancer Res, 23(8):1988-1997.
Kim, S.H. et al. (2015) "A New Germline ALA641THR Variant in the Transmembrane Domain of the RET Gene Associated with Medullary Thyroid Cancer" Acta Endocrinologica (Buc), 11.2:189-194.
Klempner et al. "Emergence of RET rearrangement co-existing with activated EGFR mutation in EGFR-mutated NSCLC patients who had progressed on first- or second-generation EGFR TKI" Lung Cancer, Sep. 2015, vol. 89, No. 3, pp. 357-359; abstract, p. 358, col. 1, para 2, p. 359, col. 1, para 2.

(56) References Cited

OTHER PUBLICATIONS

Kohno et al. (2013) "RET fusion gene: Translation to personalized lung cancer therapy," Cancer Sci 104(11):1396-1400.
Krampitz, G.W. and J.A. Norton (2014) "RET Gene Mutations (Genotype and Phenotype) of Multiple Endocrine Neoplasia Type 2 and Familial Medullary Thyroid Carcinoma" Cancer, 120:1920-1931.
Kuster, B. (Ed.) (2012) *Kinase Inhibitors. Methods and Protocols*. Humana Press; Chapters 1 and 2, pp. 1-44.
Latteyer, S. et al. (Mar. 2016) "A 6-Base Pair in Frame Germline Deletion in Exon 7 of RET Leads to Increased RET Phosphorylation, ERK Activation, and MEN2A" J Clin Endocrinol Metab, 101(3):1016-1022.
Le Rolle, A. et al. (2015) "Identification and characterization of RET fusions in advanced colorectal cancer" Oncotarget, 6(30):28929-28937.
Lee, M.S. et al. (2016) "Efficacy of the combination of MEK and CDK4/6 inhibitors in vitro and in vivo in KRAS mutant colorectal cancer models" Oncotarget, 7(26):39595-39608.
Lehar, J. et al. (2009) "Synergistic drug combinations improve therapeutic selectivity" Nat Biotechnol, 27(7):659-666. HHS Public Access Author Manuscript; available in PMC Jan. 1, 2010 (23 pages).
Lin, J.J. et al. (2016) "Clinical Activity of Alectinib in Advanced RET-Rearranged Non-Small Cell Lung Cancer" J Thorac Oncol, 11(11):2027-2032.
Lipson, D. et al. (2012) "Identification of new ALK and RET gene fusions from colorectal and lung cancer biopsies" Nat Med, 18(3):382-384. HHS Public Access Author Manuscript; available in PMC Feb. 6, 2014 (7 pages).
Machens, A et al. (2003) "Early Malignant Progression of Hereditary Medullary Thyroid Cancer" New Engl J Med, 349:1517-1525.
McMahon (2000) "VEGF Receptor Signaling in Tumor Angiogenesis," The Oncologist 5(suppl 1):3-10.
Mologni, L. et al. (2010) "Synthesis, structure-activity relationship and crystallographic studies of 3-substituted indolin-2-one RET inhibitors" Bioorg Med Chem, 18:1482-1496.
Mologni, L. et al. (2013) "Ponatinib is a potent inhibitor of wild-type and drug-resistant gatekeeper mutant RET kinase" Mol Cell Endocrinol, 377:1-6.
Mologni, L. et al. (2017) "RET kinase inhibitors: a review of recent patents (2012-2015)" Exp Opin Ther Patents, 27(1):91-99.
Moura, M.M. et al. (2009) "Correlation of RET somatic mutations with clinicopathological features in sporadic medullary thyroid carcinomas" Br J Cancer, 100:1777-1783.
Mulligan, L.M. (Mar. 2014) "RET revisited: expanding the oncogenic portfolio" Nat Rev Cancer, 14:173-186.
Mulligan, L.M. et al. (1995) "Genotype-phenotype correlation in multiple endocrine neoplasia type 2: report of the International RET Mutation Consortium" J Int Med, 238:343-346.
Mulligan, L.M. et al. (Jun. 3, 1993) "Germ-line mutations of the RET proto-oncogene in multiple endocrine neoplasia type 2A" Nature, 363:458-460.
NCT03037385, entitled "Phase 1 Study of BLU-667 in Patients With Thyroid Cancer, Non-Small Cell Lung Cancer, and Other Advanced Solid Tumors," ClinicalTrials.gov, Jan. 17, 2018 (8 pages).
NCT03037385, entitled "Phase 1 Study of BLU-667 in Patients With Thyroid Cancer, Non-Small Cell Lung Cancer, and Other Advanced Solid Tumors," ClinicalTrials.gov, Jan. 27, 2017 (7 pages).
NCT03037385, entitled Phase 1/2 Study of the Highly-selective RET Inhibitor, Pralsetinib (BLU-667), in Patients With Thyroid Cancer, Non-Small Cell Lung Cancer, and Other Advanced Solid Tumors (ARROW) (13 pages).
NCT04222972, entitled AcceleRET Lung Study of Pralsetinib for 1L Ret Fusion-positive, Metastatic NSCLC (11 pages).
Neal et la., "Erlotinib, cabozantinib, or erlotinib plus cabozantinib as second-line or third-line treatment of patients with EGFR wild-type advanced non-small-cell lung cancer (ECOG-ACRIN 1512): a randomised, controlled, open-label multicentre, phase 2 trial," Lancet Oncol, 2016, vol. 17, pp. 1661-1671.
Oxnard, G.R. et al. "Assessment of Resistance Mechanisms and Clinical Implications in Patients With EGFR T790M-Positive Lung Cancer and Acquired Resistance to Osimertinib." JAMA Oncol. 2018, 4(11), pp. 1527-1534.
Pinedo (2000) Translational Research: The Role of VEGF in Tumor Angiogenesis, The Oncologist 5(suppl 1):1-2.
Piotrowska et al (2018) "MA26.03 Activity of Osimertinib and the Selective RET Inhibitor BLU-667 in an EGFR-Mutant Patient with Acquired RET Rearrangement," Journal of Thoracic Oncology—IASLC 19th World Conference on Lung Cancer, Sep. 23, 2018, pp. S451-S451.
Piotrowska et al. (2018) "Landscape of Acquired Resistance to Osimertinib in EGFR-Mutant NSCLC and Clinical Validation of Combined EGFR and RET Inhibition with Osimertinib and BLU-677 for Acquired RET Fusion," Cancer Discovery 8(12):1529-1539.
Pirker, R. and M. Filipits (2015) "Alectinib in RET-rearranged non-small cell lung cancer—Another progress in precision medicine?" Transl Lung Cancer Res, 4(6):797-800.
Plaza-Menacho, I. et al. (2014) "Mechanisms of RET signaling in cancer: Current and future implications for targeted therapy" Cellular Signalling, 26:1743-1752.
Pound et al. "Is it possible to overcome issues of external validity in preclinical animal research? Why most animal models are bound to fail", J. Transl Med, Jan. 1, 2018 (Jan. 1, 2018), pp. 1-8, XP093000231, DOI: 10.1186/s12967-018-1678-1 Retrieved from the Internet: URL:https://www.researchgate.net/publication/328793141_1s_it_possible_to_overcome_issues_of_external_validity_in_preclinical_animal_research_Why_most_animal_models_are_bound_to_fail [retrieved on Nov. 21, 2022].
Qi, X. et al. (2015) "RET mutation p.S891A in a Chinese family with familial medullary thyroid carcinoma and associated cutaneous amyloidosis binding OSMR variant p.G513D" Oncotarget, 6(32):33993-34003.
Rahal, R. (Apr. 18, 2016) "The development of potent, selective RET inhibitors" Slides of a Presentation at the American Association for Cancer Research (AACR) Annual Meeting, Apr. 16-20, 2016, New Orleans (15 pages).
Rahal, R. et al. "BLU-667 is a Potent and Highly Selective RET Inhibitor Being Developed for RET—Driven Cancers," Poster B151, Blueprint Medicines Corporation (1 page).
Rahal, R. et al. (2016) "The development of potent, selective RET inhibitors that target both wild-type RET and prospectively identified resistance mutations to multi-kinase inhibitors" Abstract submitted to the American Association for CancerResearch (AACR) Annual Meeting, Apr. 16-20, 2016, New Orleans; submission date Dec. 1, 2015 (2 pages).
Ramalingam et al. "Osimertinib As First-Line Treatment of EGFR Mutation-Positive Advanced Non-Small-Cell Lung Cancer" Journal Of Clinical Oncology, Mar. 20, 2018, vol. 36, No. 9, p. 841-849; abstract.
Reagan-Shaw et al. (2007) "Dose translation from animal to human studies revisited" The FASEB Journal, 22:659-661.
Reckamp et al. (2014) "Phase II trial of XL184 (cabozantinib) plus erlotinib in patients (pts) with advanced EGFR-mutant non-small cell lung cancer (NSCLC) with progressive disease (PD) on epidermal growth factor receptor (EGFR) tyrosine kinase inhibitor (TKI) therapy: A California Cancer Consortium phase II trial (NCI 9303)," Journal of Clinical Oncology 32(15)8014 4 pages.
Reckamp, K. L. et al. "Abstract 936: Analysis of cell-free DNA from 32,991 advanced cancers reveals novel co-occurring activating RET alterations and oncogenic signaling pathway aberrations." Cancer Research. Pubished Jul. 2018. Proceedings: AACR Annual Meeting 2018; Apr. 14-18, 2018; Chicago, IL. Retrieved from the internet URL: "<https://cancerres.aacrjournals.org/content/78/13_Supplement/936>" (3 pages).
Robinett, R.G. et al. (2007) "The discovery of substituted 4-(3-hyroxyanilino)-quinolines as potent RET kinase inhibitors" Bioorg Med Chem Lett, 17:5886-5893.
Robinson B. G. et al. "Vandetanib (100 mg) in Patients with Locally Advanced or Metastatic Hereditary Medullary Thyroid Cancer," Journal of Clinical En Doc Ri No Logy and Metabolism, vol. 95, No. 6, Jun. 1, 2010 (Jun. 1, 2010), pp. 2664-2671, XP055599340.

(56) References Cited

OTHER PUBLICATIONS

Romei, C. et al. (Apr. 2016) "A comprehensive overview of the role of the RET proto-oncogene in thyroid carcinoma" Nat Rev Endocrinol, 12:192-202.
Russian Search Report dated Jan. 13, 2023, in Russian Patent Application No. 2020135917, Russian National Stage of International Patent Application No. PCT/US2019/025655, filed Apr. 3, 2019, by Blueprint Medicines Corp.
Saito, M. et al. (Jun. 2016) "Gene aberrations for precision medicine against lung adenocarcinoma" Cancer Sci, 107(6):713-720.
Sarker, D. and P. Workman (2007) "Pharmacodynamic Biomarkers for Molecular Cancer Therapeutics" Adv Cancer Res, 96:213-268.
Schrock, A.B. et al. "Receptor Tyrosine Kinase Fusions and BRAF Kinase Fusions are Rare but Actionable Resistance Mechanisms to EGFR Tyrosine Kinase Inhibitors." Translational Oncology, 2018, 13 (9) pp. 1312-1323.
Scollo, C. et al. (2016) "A novel RET gene mutation in a patient with apparently sporadic pheochromocytoma" Endocr J, 63(1):87-91.
Sentürk et al. (2020) "Quantitative bioanalytical assay for the selective RET inhibitors selpercatinib and pralsetinib in mouse plasma and tissue homogenates using liquid chromatography-tandem mass spectrometry," Journal of Chromatography B 1147:122131 8 pages.
Silva, A.L. et al. (2015) "Identification and characterization of two novel germline RET variants associated with medullary thyroid carcinoma" Endocrine, 49:366-372.
Singapore Written Opinion dated Dec. 13, 2021, in Singapore Patent Application No. 11202009681Y, Singapore National Stage of International Patent Application No. PCT/US2019/025655, filed Apr. 3, 2019, by Blueprint Medicines Corp.
Smith et al., "Role of ERBB signaling in RET-rearranged lung cancer and contribution of EGFR amplification to cabozantinib resistance," Journal of Clinical Oncology, 2017, vol. 35, No. 15_suppl, Abstract No. 11583.
Stransky, N. et al. (2014) "The landscape of kinase fusions in cancer" Nat Commun, 5:4846 (10 pages).
Subbiah et al. "Clinical activity and safety of the RET inhibitor pralsetinib in patients with RET fusion-positive solid tumours: update from the ARROW trial", ASCO, Jun. 4, 2021 (Jun. 4, 2021), pp. 1-1, XP093000210, Retrieved from the Internet: URL:https://ascopubs.org/doi/abs/10.1200/JCO.2021 .39.15_suppl.3079 [retrieved on Nov. 21, 2022].
Subbiah et al. Abstract CT043 "Highly potent and selective RET inhibitor, BLU-667, achieves proof of concept in a phase I study of advanced, RET-altered solid tumors," Cancer Research vol. 78, No. 13, Supplement 1 Jul. 2018 (Jul. 2018), XP002792435, Proceedings: AACR Annual Meeting 2018; Apr. 14-18, 2018; Chicago, IL. Retrieved from the Internet: URL:http://cancerres.aacrjournals.org/cont ent/78/13Supplement/CT043 [retrieved on Jun. 26, 2019].
Subbiah V. et al. "Precision Targeted Therapy with BLU-667 for RET-Driven Cancers," Cancer Discovery, vol. 8, No. 7, Apr. 15, 2018 (pp. 836-849).
Subbiah, V. et al. (Jul. 2015) "Systemic and CNS activity of the RET inhibitor vandetanib combined with the mTOR inhibitor everolimus in KIF5B-RET re-arranged Non-Small Cell Lung Cancer with brain metastases" Lung Cancer, 89(1):76-79. HHS Public Access Author Manuscript; available in PMC Aug. 25, 2016 (10 pages).
Suehara, Y. et al. (Dec. 15, 2012) "Identification of KIF5B-RET and GOPC-ROS1 fusions in lung adenocarcinomas through a comprehensive mRNA-based screen for tyrosine kinase fusions" Clin Cancer Res, 18(24):6599-6608. HHS Public Access AuthorManuscript; available in PMC Nov. 17, 2014 (18 pages).
Suzuki, M. et al. (Jul. 2013) "Identification of a lung adenocarcinoma cell line with CCDC6-RET fusion gene and the effect of RET inhibitors in vitro and in vivo" Cancer Sci, 104(7):896-903.
Takeuchi, K. et al. (Mar. 2012) "RET, ROS1 and ALK fusions in lung cancer" Nat Med, 18(3):378-381.
Tan, D.S. et al. (2009) "Biomarker-Driven Early Clinical Trials in Oncology" Cancer J, 15(5):406-420.
Thackaberry et al. (2012) "Non-clinical toxicological considerations for pharmaceutical salt selection," Expert Opin. Drug Metab. Toxicol. 8(11):1419-1433.
Touat, M. et al. (2015) "Targeting FGFR Signaling in Cancer" Clin Cancer Res, 21(12):2684-2694.
U.S. Nat'l Library of Med., A Phase 1 Trial of Vandetanib (a Multi-kinase Inhibitor of EGFR, VEGFR and RET Inhibitor) in Combination With Everolimus (an mTOR Inhibitor) in Advanced Cancer, ClinicalTrials.gov,https://clinicaltrials.gov/ct2/show/NCT01582191 (last updated Jul. 3, 2018) (7 pages).
U.S. Nat'l Library of Med., Phase 1 Study of the Highly-selective RET Inhibitor BLU-667 in Patients With Thyroid Cancer, Non-Small Cell Lung Cancer, and Other Advanced Solid Tumors, ClinicalTrials.gov, https://clinicaltrials.gov/ct2/show/NCT03037385(last updated Jun. 27, 2018) (8 pages).
Wakelee et al. (2017) "A phase Ib/II study of cabozantinib (XL184) with or without erlotinib in patients with non-small cell lung cancer," Cancer Chemother Pharmacol 79:923-932.
Wang et al., "Abstract 4110: Combinatory approaches targeting EGFR, HER2 and c-MET in recurrent SCCHN," Cancer Res, 2017, vol. 77, No. 13_Supplement, Abstract No. 4110.
Wang, L. et al. (2012) "Identification of a Novel, Recurrent HEY1-NCOA2 Fusion in Mesenchymal Chondrosarcoma based on a Genome-wide Screen of Exon-level Expression Data" Genes Chromosomes Cancer, 51(2):127-139. HHS Public Access Author Manuscript; available in PMC Feb. 1, 2013 (24 pages).
Wang, R. et al. (Dec. 10, 2012) "RET Fusions Define a Unique Molecular and Clinicopathologic Subtype of Non-Small-Cell Lung Cancer" J Clin Oncol, 30(35):4352-4359.
Wells, S.A. et al. (2015) "Revised American Thyroid Association Guidelines for the Management of Medullary Thyroid Carcinoma" Thyroid, 25(6):567-610.
Zhang et al., "Activation of the AXL kinases causes resistance to EGFR-targeted therapy in lung cancer," Nature Genetics, 2012, vol. 44, No. 8, pp. 852-860.
Gainor et al., "Pralsetinib for RET fusion-positive non-small-cell lung cancer (ARROW): a multi-cohort, open-label, phase 1/2 study," Lancet Oncology, 2021, 22(7), 959-969 (supplementary appendix) (218 pages).
Gainor et al., "Pralsetinib for RET fusion-positive non-small-cell lung cancer (ARROW): a multi-cohort, open-label, phase 1/2 study," Lancet Oncology, 2021, 22(7), 959-969.
Konno, "Effect of polymers on stabilization of drugs in solid dispersions," Pharmaceutics, 2011, 71(2), pp. 109-113.
Pharmaceutical Dosage Forms: Tablets.—3rd ed., vol. 2 /edited by Larry L. Augsburger, Stephen W. Hoag, 2008, Chapter 6 (38 pages).
Phase 1 Cancer Clinical Trials: A Practical Guide, Second Edition, Eds. E.A. Eisenhauer et al., Chapter 4, Basics of Phase I Design: First-in-Human Studies, Oxford University Press, 2015 (37 pages).
Tanno et al., "Evaluation of Hypromellose Acetate Succinate (HPMCAS) as a Carrier in Solid Dispersions," Drug Dev. Ind. Pharm., 2004, vol. 30, No. 1, pp. 9-17 (10 pages).

* cited by examiner

METHOD OF PREPARING PRALSETINIB

CROSS-REFERENCE

This application is a U.S. National Stage Application of International Patent Application No. PCT/US2021/061754, filed on Dec. 3, 2021, which claims the benefit of and priority to U.S. Provisional Application No. 63/121,330, filed on Dec. 4, 2020, the disclosure of each of which is incorporated herein by reference in its entirety.

BACKGROUND

Targeting oncogenic driver kinases with specifically tailored inhibitors has transformed the management of a variety of hematologic malignancies and solid tumors. The receptor tyrosine kinase, rearranged during transfection (RET), is an oncogenic driver activated in multiple cancers including non-small cell lung cancer (NSCLC), medullary thyroid cancer (MTC), and papillary thyroid cancer (PTC). Oncogenic RET alterations promote ligand-independent, constitutive RET kinase activation, which drives tumorigenesis (e.g., RET fusions are seen in 10%-20% of PTC, 1%-2% of NSCLC, and multiple other cancer subtypes).

Pralsetinib is a highly potent and selective RET inhibitor designed to overcome these limitations, through the highly potent and selective targeting of oncogenic RET alterations, including the most prevalent RET fusions and certain RET activating mutations. Pralsetinib can also be referred to as: (cis)-N-((S)-1-(6-(4-fluoro-1H-pyrazol-1-yl)pyridin-3-yl)ethyl)-1-methoxy-4-(4 methyl-6-(5-methyl-1H-pyrazol-3-ylamino)pyrimidin-2-yl)cyclohexanecarboxamide, and has the following chemical structure:

(X)

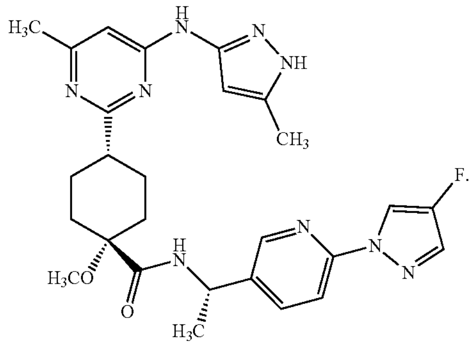

Clinical trials under NCT03037385, entitled "Phase 1/2 Study of the Highly-selective RET Inhibitor, Pralsetinib (BLU-667), in Patients With Thyroid Cancer, Non-Small Cell Lung Cancer, and Other Advanced Solid Tumors (ARROW)," and NCT04222972, entitled "AcceleRET Lung Study of Pralsetinib for 1 L RET Fusion-positive, Metastatic NSCLC" are underway.

Pralsetinib is disclosed as one of many RET inhibitor compounds in patent publication WO2017/079140. The successful commercialization of a new therapeutic agent requires an efficient process for preparing the agent in high yield and purity. Therefore, there still exists a need for improved processes for preparing pralsetinib that are more efficient and suitable for large scale manufacturing processes.

SUMMARY OF THE DISCLOSURE

In one aspect, the present disclosure provides a compound of Formula (I):

(I)

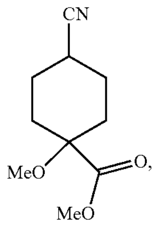

or a salt thereof.

The compound of Formula (I) is a compound of Formula (Ia):

(Ia)

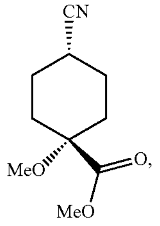

or a salt thereof.

The compound of Formula (I) is a compound of Formula (Ib):

(Ib)

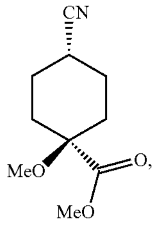

or a salt thereof.

In another aspect, the present disclosure provides a compound of Formula (II):

(II)

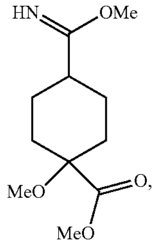

or a salt thereof.

The compound of Formula (II) is a compound of Formula (IIa):

(IIa)

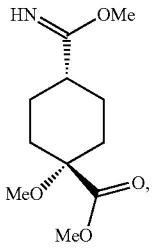

or a salt thereof.

The compound of Formula (II) is a compound of Formula (IIb):

(IIb)

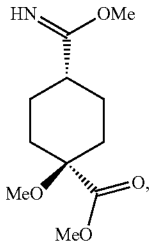

or a salt thereof.

The present disclosure provides, in part, a compound of Formula (III):

(III)

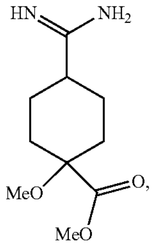

or a salt thereof.

The compound of Formula (III) is a compound of Formula (IIIa):

(IIIa)

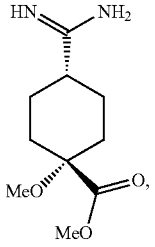

or a salt thereof.

The compound of Formula (III) is a compound of Formula (IIIb):

(IIIb)

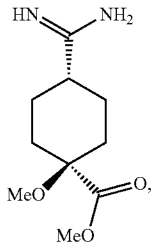

or a salt thereof.

Also provided herein, is an isomeric mixture of cis and trans isomers of a compound of Formula (III):

(III)

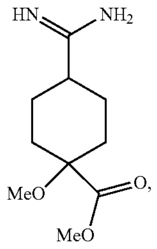

or a salt thereof, wherein the cis isomer is a compound of Formula (IIIa):

(IIIa)

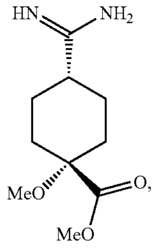

or a salt thereof, and the trans isomer is a compound of Formula (IIIb):

(IIIb)

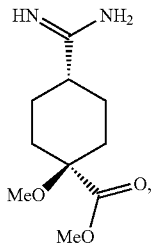

or a salt thereof, wherein the ratio of the cis isomer to the trans isomer is greater than or equal to about 4 to 1.

Provided herein, in part, is a compound of Formula (IVa):

(IVa)

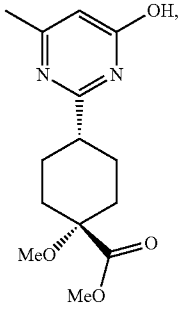

or a salt or a tautomer thereof.

Also provided herein is a compound of Formula (IVb):

(IVb)

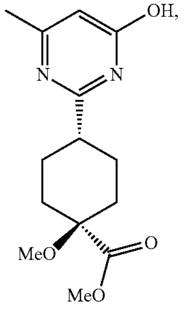

or a salt or a tautomer thereof.

The present disclosure also provides an isomeric mixture of cis and trans isomers of a compound of Formula (IV):

(IV)

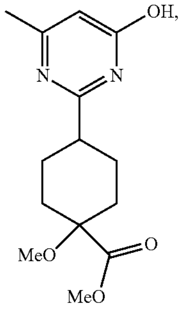

or a salt thereof, wherein the cis isomer is a compound of Formula (IVa):

(IVa)

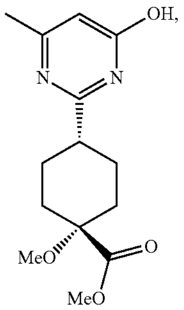

or a salt thereof and the trans isomer is a compound of Formula (IVb):

(IVb)

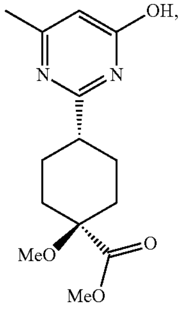

or a salt thereof, wherein the ratio of the cis isomer to the trans isomer is greater than or equal to about 4 to 1.

In another aspect, the present disclosure provides a compound of Formula (V-1):

(V-1)

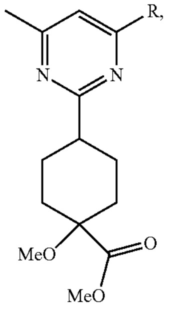

or a salt thereof, wherein R is an activating group.

In some embodiments, the compound of Formula (V-1) is a compound of Formula (V):

(V)

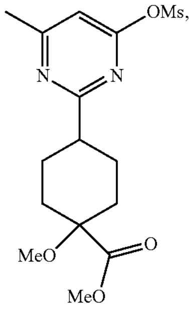

or a salt thereof.

The compound of Formula (V) is a compound of Formula (Va):

(Va)

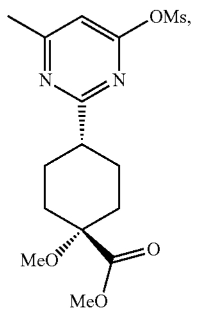

or a salt thereof.

The compound of Formula (V) is a compound of Formula (Vb):

(Vb)

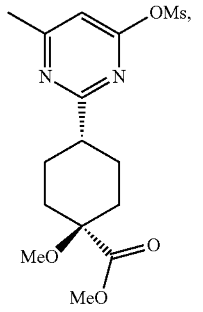

or a salt thereof.

Also provided herein is an isomeric mixture of cis and trans isomers of a compound of Formula (V):

(V)

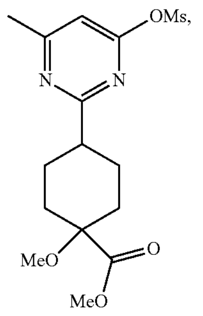

or a salt thereof, wherein the cis isomer is a compound of Formula (Va):

(Va)

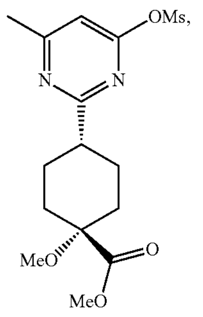

or a salt thereof and the trans isomer is a compound of Formula (Vb):

(Vb)

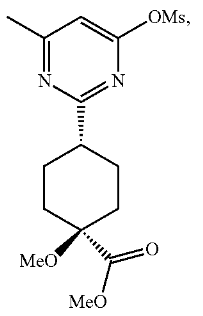

or a salt thereof, wherein the ratio of the cis isomer to the trans isomer is greater than or equal to about 4 to 1.

Provided herein, in part, is a composition comprising a compound of Formula (VI):

(VI)

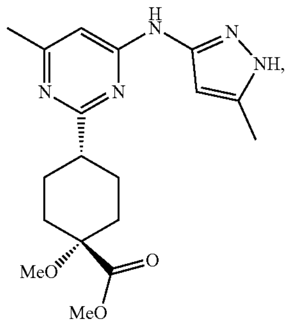

or a salt thereof, wherein the composition is substantially free of a compound of Formula (VIa):

(VIa)

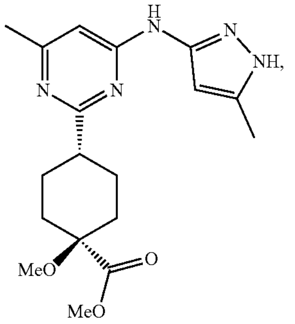

or a salt thereof.

The present disclosure also provides a composition comprising a compound of Formula (VII):

(VII)

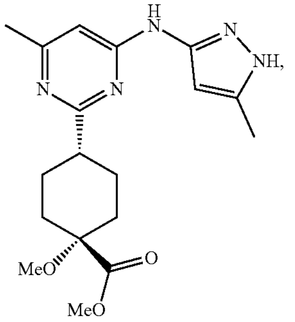

or a salt thereof, wherein the composition is substantially free of the compound of Formula (VIIa):

(VIIa)

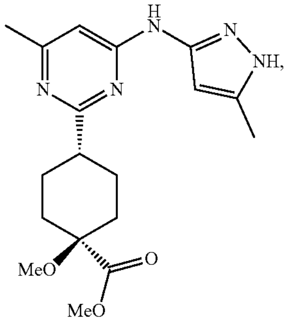

or a salt thereof.

In another aspect, provided herein is a process of preparing a composition comprising a mixture of cis and trans isomers of a compound of Formula (IV):

(IV)

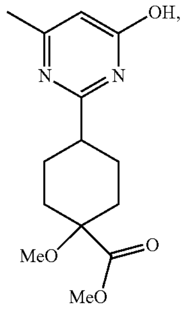

or a salt or a tautomer thereof, wherein the process comprises:

(a) reacting a compound of Formula (II):

(II)

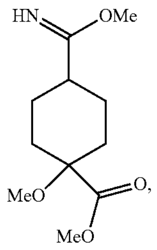

or a salt thereof with an ammonium source in the presence of a solvent, thereby producing a compound of Formula (III):

(III)

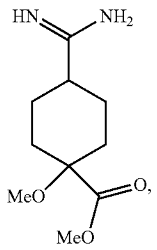

or a salt thereof; and (b) reacting a compound of Formula (III) with alkyl acetoacetate, thereby producing a composition comprising a mixture of cis and trans isomers of a compound of Formula (IV) having a greater amount of the cis isomer, Formula (IVa):

(IVa)

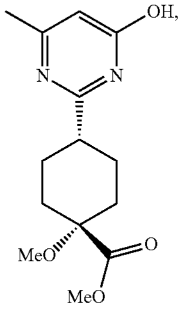

or a salt thereof as compared to the trans isomer, Formula (IVb):

(IVb)

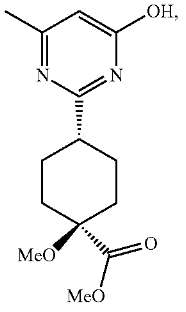

or a salt thereof.

The present disclosure provides, in part, a process of preparing a composition comprising a mixture of cis and trans isomers of a compound of Formula (III) or a salt thereof with an increased ratio of the cis isomer to the trans isomer:

(III)

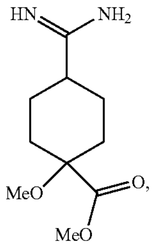

wherein the cis isomer is a compound of Formula (IIIa):

(IIIa)

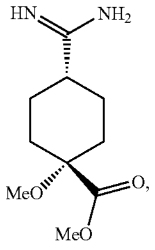

or a salt thereof and the trans isomer is a compound of Formula (IIIb):

(IIIb)

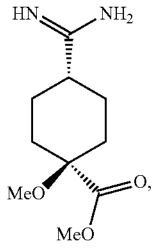

or a salt thereof comprising reacting a compound of Formula (II):

(II)

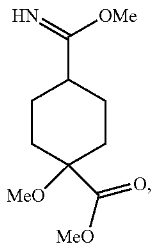

or a salt thereof with an ammonium source in the presence of a solvent, thereby producing a composition comprising a mixture of cis and trans isomers of a compound of Formula (III) with an increased ratio of the cis isomer to the trans isomer.

Provided herein, in part, is a process of preparing a compound of Formula (X):

(X)

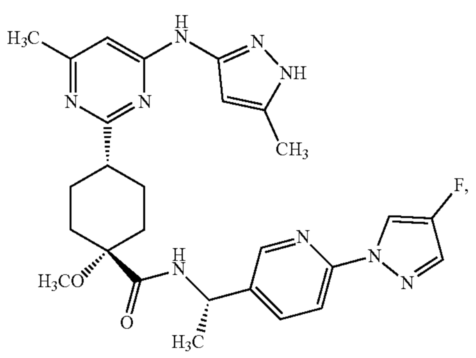

or a salt thereof, comprising the steps of:

(a) reacting a compound of Formula (II):

(II)

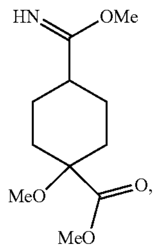

or a salt thereof with an ammonium source, e.g., $NH_3$ or $NH_4Cl$, in the presence of a solvent, thereby producing a compound of Formula (III):

(III)

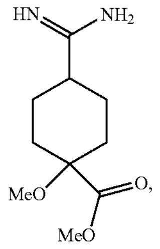

or a salt thereof, (b) reacting a compound of Formula (III) or a salt thereof with alkyl acetoacetate, thereby producing an isomeric mixture of a compound of Formula (IV) or a salt thereof:

(IV)

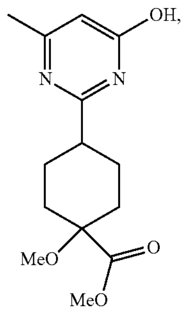

wherein the isomeric mixture of the compound of Formula (IV) has a greater amount of the cis isomer, Formula (IVa):

(IVa)

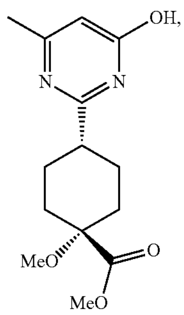

as compared to the trans isomer, Formula (IVb):

(IVb)

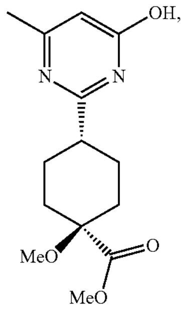

or a salt thereof:

(c) purifying the isomeric mixture of the compound of Formula (IV) to obtain the compound of Formula (IVa);

(d) reacting the compound of Formula (IVa) or a salt thereof with an activating agent, thereby providing a compound of Formula (V-1a):

(V-1a)

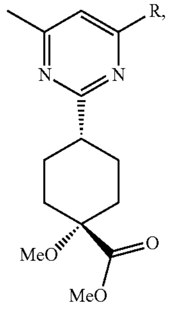

or a salt thereof, (e) reacting the compound of Formula (V-1a) or a salt thereof with 5-methyl-3-pyrazolamine, thereby providing a compound of Formula (VI):

(VI)

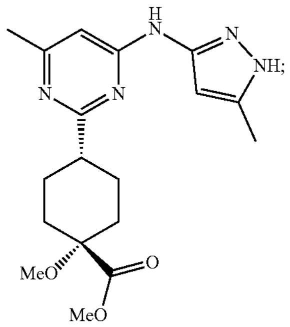

or a salt thereof;

(f) reacting the compound of Formula (VI) or a salt thereof with a base, thereby providing a compound of Formula (VII):

(VII)

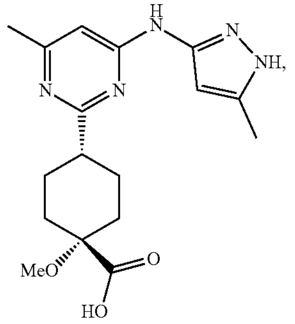

or a salt thereof;

(g) reacting the compound of Formula (VII) or a salt thereof with a compound of Formula (VIII):

(VIII)

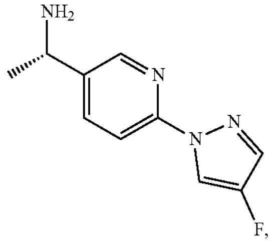

or a salt thereof, thereby providing the compound of Formula (X) or a salt thereof.

Also provided herein, in part, is a process of preparing a compound of Formula (X):

(X)

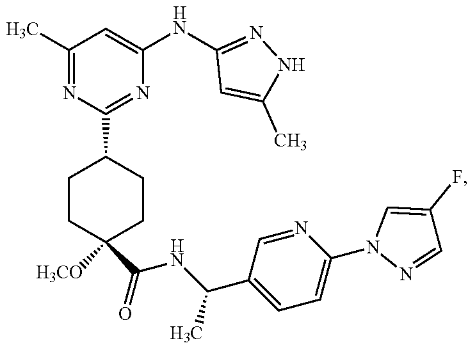

or a salt thereof, comprising the steps of:

(a) reacting a compound of Formula (IVa):

(IVa)

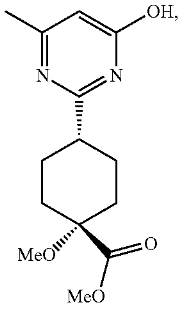

or a salt thereof with an activating agent, thereby providing a compound of Formula (V-1a):

(V-1a)

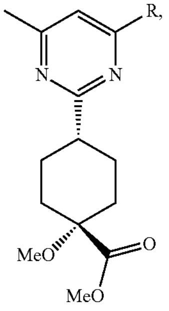

or a salt thereof;

(b) reacting the compound of Formula (V-1a) or a salt thereof with 5-methyl-3-pyrazolamine, thereby providing a compound of Formula (VI):

(VI)

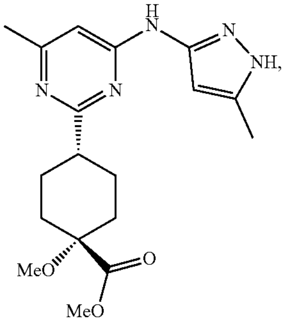

or a salt thereof;

(c) reacting the compound of Formula (VI) or a salt thereof with a base, thereby providing a compound of Formula (VII):

(VII)

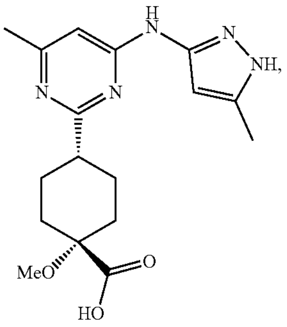

or a salt thereof; and (d) reacting a compound of Formula (VII) or a salt thereof with a compound of Formula (VIII):

(VIII)

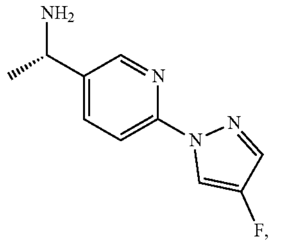

or a salt thereof, thereby providing a salt of a compound of Formula (X).

Also provided herein is a process of preparing a composition comprising a mixture of cis and trans isomers of a composition of Formula (X) having a majority of the cis isomer configuration, (X)

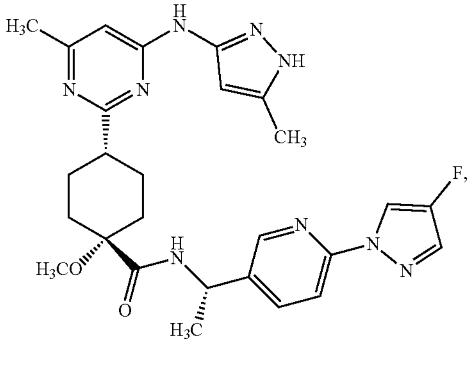

the process comprising:

reacting a compound of Formula (VII):

(VII)

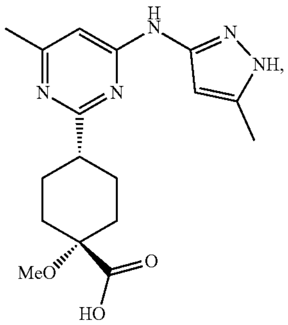

or a salt thereof, with a compound of Formula (VIII):

(VIII)

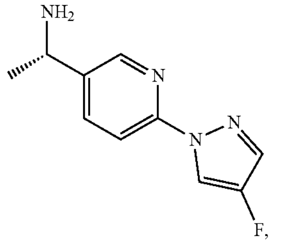

or a salt thereof, thereby providing a composition comprising a mixture of cis and trans isomers of the compound of Formula (X) having a majority of a cis isomer configuration.

Provided herein, in part, is a geometric isomeric mixture comprising a compound of Formula (X):

(X)

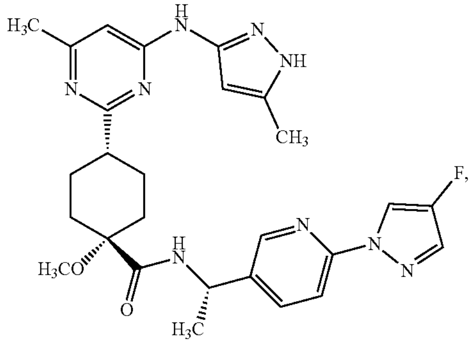

prepared with a process as described herein, wherein the geometric isomer mixture has a cis:trans molar ratio of from about 4:1 to about 99:1.

DETAILED DESCRIPTION

The present disclosure provides, in part, novel compounds and compositions useful for preparing pralsetinib. Also provided herein are processes for preparing pralsetinib that result in a higher stereoselectivity and yield of pralsetinib and therefore are more suitable for large scale manufacturing processes as compared to known methods.

Definitions

"Alkyl" refers to a monovalent radical of a saturated straight or branched hydrocarbon, such as a straight or branched group of 1-12, 1-10, or 1-6 carbon atoms, referred to herein as C1-C12 alkyl, C1-C10 alkyl, and C1-C6 alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

Certain compounds of the present disclosure may exist in particular geometric or stereoisomeric forms. The present disclosure contemplates all such compounds, including cis- and trans-isomers, R- and S-enantiomers, diastereomers, (D)-isomers, (L)-isomers, the racemic mixtures thereof, and other mixtures thereof, as falling within the scope of the disclosure.

Geometric isomers can also exist in the compounds of the present disclosure. The present disclosure encompasses the various geometric isomers and mixtures thereof resulting from the arrangement of substituents around a ring (e.g., carbocyclic ring). The arrangement of substituents around a ring (e.g., carbocyclic ring) are designated as "cis" or "trans." The term "cis" represents substituents on the same side of the plane of the ring and the term "trans" represents substituents on opposite sides of the plane of the ring. If there are two substituents on a carbon atom of a ring, the substituents are ranked according to Cahn-Ingold Prelog priority rules (to assign the priority of the atom/group based on the atomic number of that atom. A higher atomic number has a higher priority). Mixtures of compounds wherein the substituents are disposed on both the same and opposite sides of plane of the ring can be designated "cis/trans."

The term "geometric isomeric mixture" as used herein refers to a mixture of the cis and trans isomers of a compound disclosed herein.

Unless otherwise indicated, when a disclosed compound is named or depicted by a structure without specifying the stereochemistry it is understood to represent all possible stereoisomers of the compound (e.g., all cis and trans isomers).

The compounds described herein may also contain unnatural proportions of atomic isotopes at one or more of the atoms that constitute such compounds. For example, the compounds may be radiolabeled with radioactive isotopes, such as for example deuterium (2H), tritium (3H), carbon-13 (13C), or carbon-14 (14C). All isotopic variations of the compounds disclosed herein, whether radioactive or not, are intended to be encompassed within the scope of the present disclosure. In addition, all tautomeric forms of the compounds described herein are intended to be within the scope of the disclosure.

The compound disclosed herein may be useful as the free base or as a salt. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", J. Pharm. Sci. 66:1-19.)

The term "tautomers" refer to compounds that are interchangeable forms of a particular compound structure, and that vary in the displacement of hydrogen atoms and electrons. Thus, two structures may be in equilibrium through the movement of n electrons and an atom (usually H).

The term "activating agent" refers to an agent that increases the propensity of the molecule to undergo a specific chemical reaction.

Unless otherwise indicated, all numbers expressing quantities of ingredients, reaction conditions, data points (e.g., geometric isomeric ratio, temperature, angles, etc.) and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present disclosure.

Unless otherwise indicated, all numerical ratios used herein to describe isomeric mixtures are to be understood as molar ratios.

Compounds and Compositions

In one aspect, the present disclosure provides a compound of Formula (I):

(I)

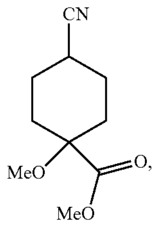

or a salt thereof.

The compound of Formula (I) is a compound of Formula (Ia):

(Ia)

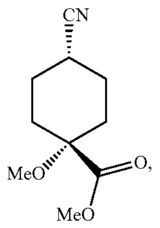

or a salt thereof.

The compound of Formula (I) is a compound of Formula (Ib):

(Ib)

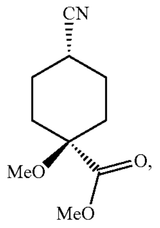

or a salt thereof.

In another aspect, the present disclosure provides a compound of Formula (II):

(II)

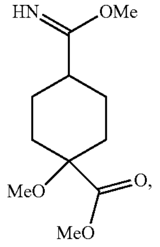

or a salt thereof.

The compound of Formula (II) a compound of Formula (IIa):

(IIa)

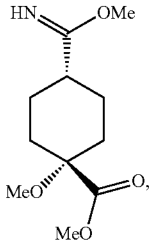

or a salt thereof.

The compound of Formula (II) is a compound of Formula (IIb):

(IIb)

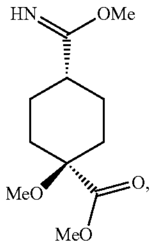

or a salt thereof.

The present disclosure provides, in part, a compound of Formula (III):

(III)

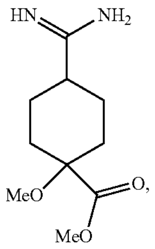

or a salt thereof.

The compound of Formula (III) is a compound of Formula (IIIa):

(IIIa)

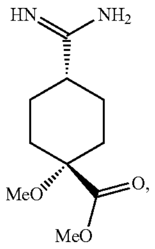

or a salt thereof.

The compound of Formula (II) is a compound of Formula (IIIb):

(IIIb)

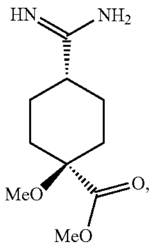

or a salt thereof.

Also provided herein, is an isomeric mixture of cis and trans isomers of a compound of Formula (III):

(III)

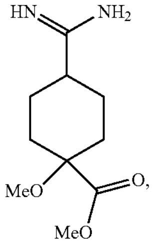

or a salt thereof, wherein the cis isomer is a compound of Formula (IIIa):

(IIIa)

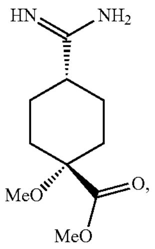

or a salt thereof, and the trans isomer is a compound of Formula (IIIb):

(IIIb)

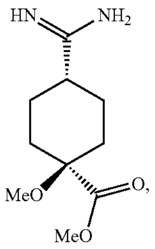

or a salt thereof, wherein the ratio of the cis isomer to the trans isomer is greater than or equal to about 4 to 1, greater than or equal to about 5:1, greater than or equal to about 6:1, greater than or equal to about 7:1, greater than or equal to about 8:1, greater than or equal to about 9:1, greater than or equal to about 3:1, greater than or equal to about 2:1, greater than or equal to about 75:25, greater than or equal to about 7:3, greater than or equal to about 85:15, greater than or equal to about 65:35, or greater than or equal to about 3:2.

Provided herein, in part, is a compound of Formula (IV):

(IV)

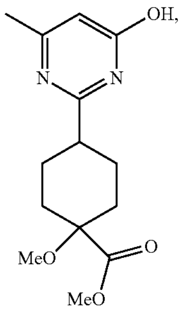

or a salt thereof.

The compound of Formula (IV) a compound of Formula (IVa):

(IVa)

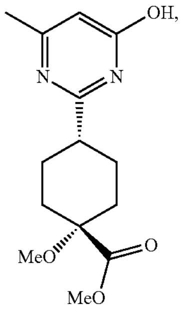

or a salt thereof.

The compound of Formula (IV) is a compound of Formula (IVb):

(IVb)

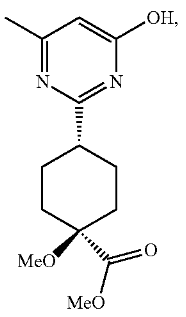

or a salt thereof.

The present disclosure also provides an isomeric mixture of cis and trans isomers of a compound of Formula (IV):

(IV)

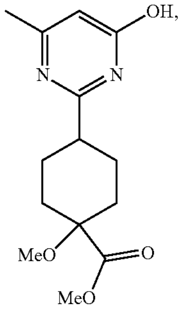

or a salt thereof, wherein the cis isomer is a compound of Formula (IVa):

(IVa)

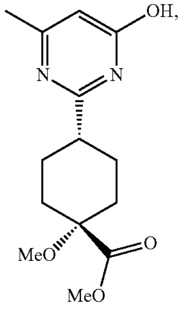

and the trans isomer is a compound of Formula (IVb):

(IVb)

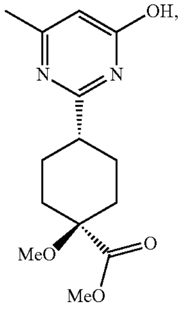

or a salt thereof, wherein the ratio of the cis isomer to the trans isomer is greater than or equal to about 4 to 1, greater than or equal to about 5:1, greater than or equal to about 6:1, greater than or equal to about 7:1, greater than or equal to about 8:1, greater than or equal to about 9:1, greater than or equal to about 3:1, greater than or equal to about 2:1, greater than or equal to about 75:25, greater than or equal to about 7:3, greater than or equal to about 85:15, greater than or equal to about 65:35, or greater than or equal to about 3:2.

In another aspect, the present disclosure provides a compound of Formula (V-1):

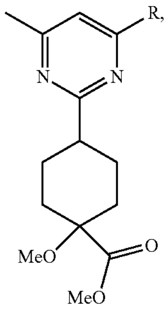

(V-1)

or a salt thereof, wherein R is an activating group.

In some embodiments, the activating group is a chemical group introduced to activate the alcohol for a substitution reaction. In certain embodiments, R is selected from the group consisting of —Cl, —O-methanesulfonyl, —O-p-toluenesulfonyl, a phosphite ester, chlorosulfite, and triflate.

In some embodiments, the compound of Formula (V-1) is a compound of Formula (V-1a):

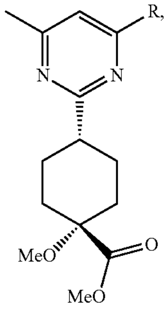

(V-1a)

or a salt thereof, wherein R is an activating group.

In other embodiments, the compound of Formula (V-1) is a compound of Formula (V-1b):

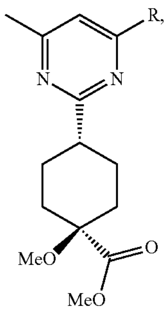

(V-1b)

or a salt thereof, wherein R is an activating group.

In some embodiments, the compound of Formula (V-1) is a compound of Formula (V):

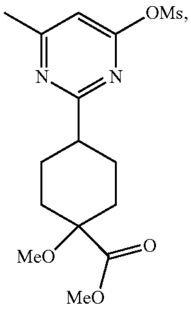

(V)

or a salt thereof.

The compound of Formula (V) is a compound of Formula (Va):

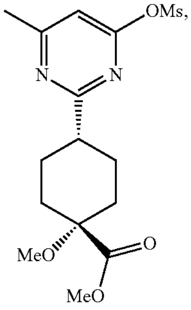

(Va)

or a salt thereof.

The compound of Formula (V) is a compound of Formula (Vb):

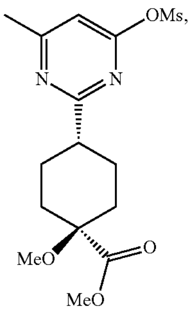

(Vb)

or a salt thereof.

Also provided herein is an isomeric mixture of cis and trans isomers of a compound of Formula (V):

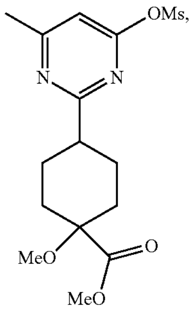

(V)

or a salt thereof, wherein the cis isomer is a compound of Formula (Va):

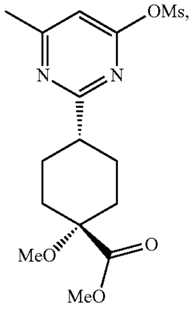

(Va)

or a salt thereof and the trans isomer is a compound of Formula (Vb):

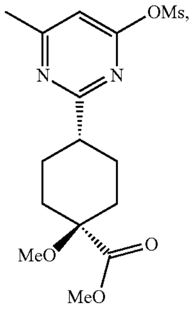

(Vb)

or a salt thereof, wherein the ratio of the cis isomer to the trans isomer is greater than or equal to about 4 to 1, greater than or equal to about 5:1, greater than or equal to about 6:1, greater than or equal to about 7:1, greater than or equal to about 8:1, greater than or equal to about 9:1, greater than or equal to about 3:1, greater than or equal to about 2:1, greater than or equal to about 75:25, greater than or equal to about 7:3, greater than or equal to about 85:15, greater than or equal to about 65:35, or greater than or equal to about 3:2.

Provided herein, in part, is a composition comprising a compound of Formula (VI):

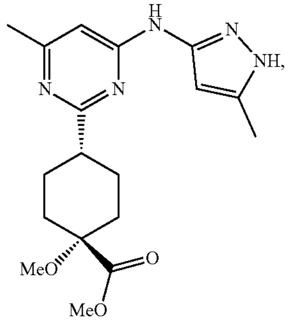

(VI)

or a salt thereof, wherein the composition is substantially free of a compound of Formula (VIa):

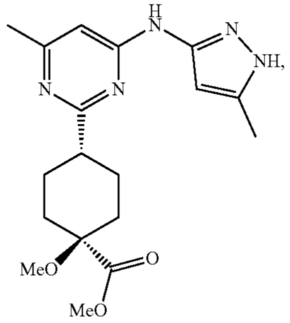

(VIa)

or a salt thereof.

In some embodiments, the composition is substantially free of the compound of Formula (VIa) or a salt thereof when the ratio of the compound of Formula (VI) or a salt thereof and the compound of Formula (VIa) or a salt thereof is greater than or equal to about 9:1, greater than or equal to about 91:9, greater than or equal to about 92:8, greater than or equal to about 93:7, greater than or equal to about 94:6, greater than or equal to about 95:5, greater than or equal to about 96:4, greater than or equal to about 97 to 3, greater than or equal to about 99:3, greater than or equal to about 99:1.

In other embodiments, the ratio of the compound of Formula (VI) or a salt thereof and the compound of Formula (VIa) or a salt thereof is detected using HPLC.

In certain embodiments, the composition comprises less than 10%, 5%, 1%, 0.5%, or 0.1% of a compound of Formula (VIa) or a salt thereof by weight of a compound of Formula (VI) or a salt thereof.

The present disclosure also provides a composition comprising a compound of Formula (VII):

(VII)

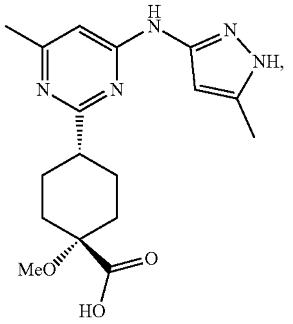

or a salt thereof, wherein the composition is substantially free of the compound of Formula (VIIa):

(VIIa)

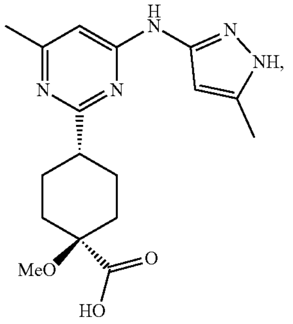

or a salt thereof.

In some embodiments, the ratio of the compound of Formula (VII) or a salt thereof and the compound of Formula (VIIa) or a salt thereof is greater than or equal to about 9:1, greater than or equal to about 91:9, greater than or equal to about 92:8, greater than or equal to about 93:7, greater than or equal to about 94:6, greater than or equal to about 95:5, greater than or equal to about 96:4, greater than or equal to about 97 to 3, greater than or equal to about 99:3, greater than or equal to about 99:1.

Process of Preparing Compounds

In another aspect, provided herein is a process of preparing a composition comprising a mixture of cis and trans isomers of a compound of Formula (IV):

(IV)

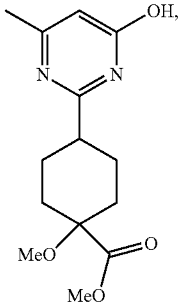

or a salt thereof, wherein the process comprises:

(a) reacting a compound of Formula (II):

(II)

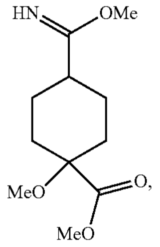

or a salt thereof with an ammonium source in the presence of a solvent, thereby producing a compound of Formula (III):

(III)

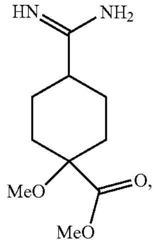

or a salt thereof; and (b) reacting a compound of Formula (III) with alkyl acetoacetate, thereby producing a composition comprising a mixture of cis and trans isomers of a compound of Formula (IV) having a greater amount of the cis isomer, Formula (IVa):

(IVa)

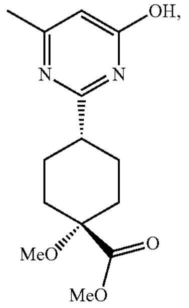

or a salt thereof as compared to the trans isomer, Formula (IVb):

(IVb)

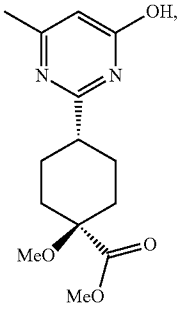

or a salt thereof.

The present disclosure provides, in part, a process of preparing a composition comprising a mixture of cis and trans isomers of a compound of Formula (III) or a salt thereof with an increased ratio of the cis isomer to the trans isomer:

(III)

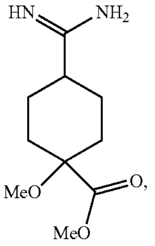

wherein the cis isomer is a compound of Formula (IIIa):

(IIIa)

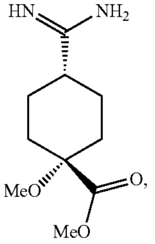

or a salt thereof and the trans isomer is a compound of Formula (IIIb):

(IIIb)

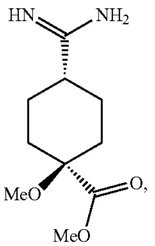

or a salt thereof, comprising reacting a compound of Formula (II):

(II)

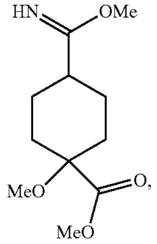

or a salt thereof with an ammonium source in the presence of a solvent, thereby producing a composition comprising a mixture of cis and trans isomers of a compound of Formula (III) with increased ratio of the cis isomer to the trans isomer.

Provided herein, in part, is a process of preparing a compound of Formula (X):

(X)

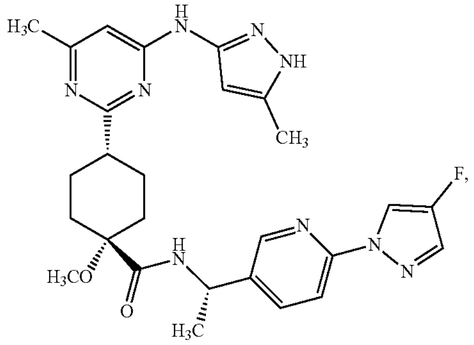

or a salt thereof, comprising the steps of:

(a) reacting a compound of Formula (II):

(II)

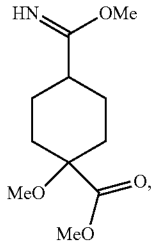

or a salt thereof with an ammonium source in the presence of a solvent, thereby producing a compound of Formula (III):

(III)

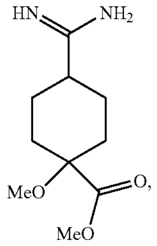

or a salt thereof, (b) reacting a compound of Formula (III) with alkyl acetoacetate, thereby producing an isomeric mixture of a compound of Formula (IV):

(IV)

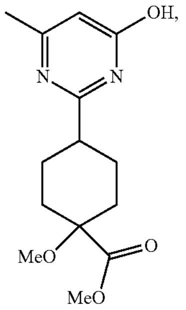

or a salt thereof, wherein the isomeric mixture of the compound of Formula (IV) has a greater amount of the cis isomer, Formula (IVa):

(IVa)

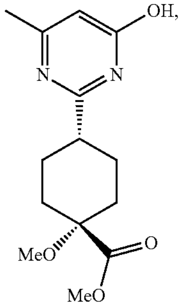

or a salt thereof, as compared to the trans isomer, Formula (IVb):

(IVb)

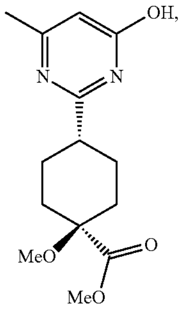

or a salt thereof:

(c) purifying the isomeric mixture of the compound of Formula (IV) or a salt thereof to obtain the compound of Formula (IVa) or a salt thereof;

(d) reacting the compound of Formula (IVa) or a salt thereof with an activating agent, thereby providing a compound of Formula (V-1a):

(V-Ia)

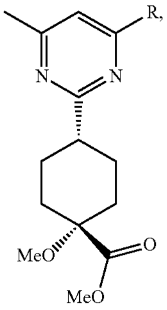

or a salt thereof, wherein R is an activating group;

(e) reacting the compound of Formula (V-1a) or a salt thereof with 5-methyl-3-pyrazolamine, thereby providing a compound of Formula (VI):

(VI)

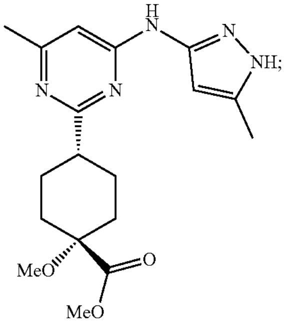

or a salt thereof;

(f) reacting the compound of Formula (VI) or a salt thereof with a base, thereby providing a compound of Formula (VII):

(VII)

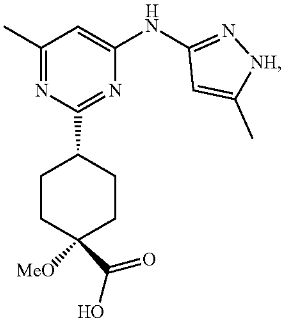

or a salt thereof;

(g) reacting the compound of Formula (VII) or a salt thereof with a compound of Formula (VIII):

(VIII)

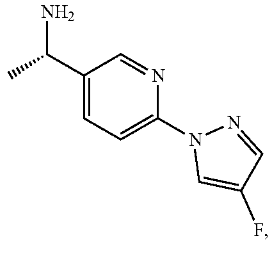

or a salt thereof, thereby providing the compound of Formula (X), or a salt thereof.

It can be appreciated that in some embodiments, reacting one compound with another can be in the presence of a solvent or an additional solvent to any solvent noted throughout or associated with a certain reacting step. For example, contemplated solvents may include appropriate solvents for each e.g., step of a contemplated process or method. In certain embodiments, R is selected from the group consisting of —Cl, —O-methanesulfonyl, —O-p-toluenesulfonyl, a phosphite ester, chlorosulfite, and triflate. In some embodiments, R is —Cl or —OMs.

In some embodiments, the activating agent is a methanesulfonyl agent and R is —OMs.

Also provided herein is a process of preparing a compound of Formula (VIII):

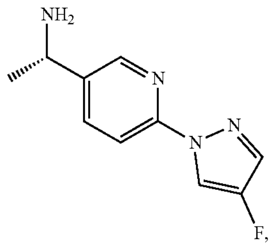

or a salt thereof, comprising the steps of:

(a) reacting a compound represented by:

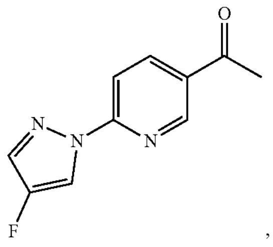

, or a salt thereof, with (R)-2-methyl-2-propanesulfinamide at between −15° C. and −25° C., thereby providing a compound represented by:

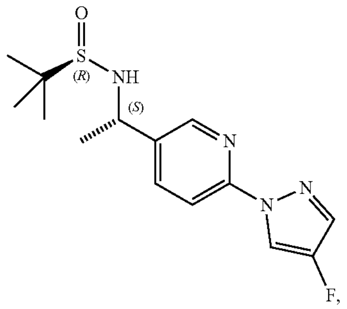

or a salt thereof; and (b) reacting the compound provided in step (a) with an acid, thereby providing the compound of Formula (VIII), or a salt thereof.

Also provided herein, in part, is a process of preparing a compound of Formula (X):

(X)

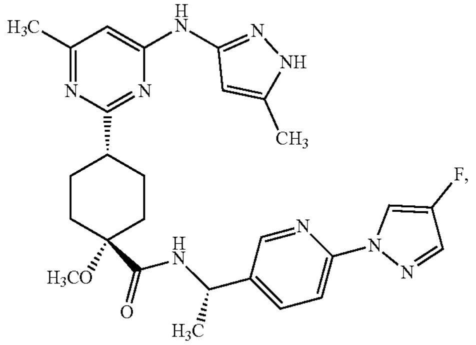

or a salt thereof, comprising the steps of:

(a) reacting a compound of Formula (IVa):

(IVa)

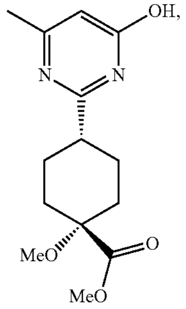

or a salt thereof with an activating agent, thereby providing a compound of Formula (V-1a):

(V-1a)

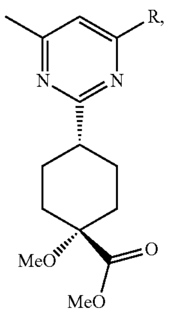

or a salt thereof, wherein R is an activating group;

(b) reacting the compound of Formula (V-1a) or a salt thereof with 5-methyl-3-pyrazolamine, thereby providing a compound of Formula (VI):

(VI)

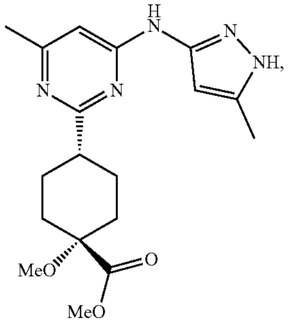

or a salt thereof;

(c) reacting the compound of Formula (VI) or a salt thereof with a base, thereby providing a compound of Formula (VII):

(VII)

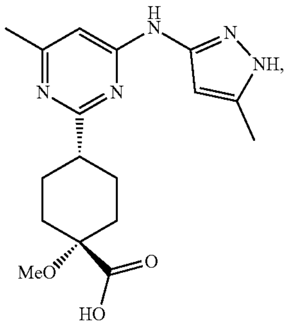

or a salt thereof; and (d) reacting a compound of Formula (VII) or a salt thereof with a compound of Formula (VIII):

(VIII)

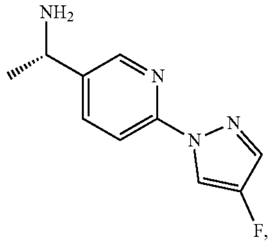

or a salt thereof, thereby providing a salt of a compound of Formula (X).

In certain embodiments, R is selected from the group consisting of —Cl, —O— methanesulfonyl, —O-p-toluenesulfonyl, a phosphite ester, chlorosulfite, and triflate. In some embodiments, R is —Cl or —OMs. In some embodiments, the activating agent is a methanesulfonyl agent and R is —OMs.

In some embodiments, the last step of the process further comprises reacting a salt of a compound of Formula (X) with a base, thereby providing a compound of Formula (X). For example, in some embodiments, the salt of a compound of Formula (X) is an HCl salt.

The contemplated ratio of the cis isomer to the trans isomer of a compound of Formula (III) may be about 4 to 1, at least 4 to 1, greater than or equal to about 4:1, about 75 to 25, at least 75 to 25, or greater than or equal to about 75 to 25. The contemplated ratio of the cis isomer to the trans isomer of a compound of Formula (IV) may be about 4 to 1, at least 4 to 1, greater than or equal to about 4 to 1, about 75 to 25, at least 75 to 25, or greater than or equal to about 75 to 25.

In certain embodiments, the reaction of a compound of Formula (II), or a pharmaceutically acceptable salt thereof with an ammonium source (such as in certain step (a) described herein) further comprises heating the solvent (for example to reflux), for example, step (a) further comprises heating the solvent to about 30° C. or to about 40° C. or more, for example, to about 50° C. or higher, e.g., about 55° C. or higher, about 60° C. or higher, about 65° C. or higher, e.g., about 70° C. or higher. In some embodiments of any of the methods herein which include reacting a compound of Formula (II) with an ammonium source in the presence of solvent, the solvent is a polar solvent in which the ammonium source is soluble, such as, for example, a polar protic solvent or a polar aprotic solvent, or a mixture thereof. In some embodiments, the solvent comprises C1-C4alkyl alcohol or mixture of alcohols. In some embodiments, the solvent is methanol, or ethanol, or propanol, or butanol, or dioxane, or a combination thereof. In some embodiments the ammonium source is ammonia or ammonium chloride. In certain embodiments, the solvent is methanol and the ammonium source is ammonia. In certain embodiments which may include any of the preceding embodiments, the compound of Formula (II) is reacted with the ammonium source in the presence of solvent at a temperature of at least 30° C., at least 40° C., at least 50° C., at least 60° C. at least 70° C., at least 80° C., between 30° C. to 100° C., between 40° C. to 90° C., between 50° C. to 80° C., between 60° C. to 80° C., or about 60° C. to about 70° C. In certain embodiments, the reaction mixture is heated to reflux. In some embodiments, the reaction mixture is heated to between about 50° C. to about 80° C. and the solvent is a C1-C4alkyl alcohol or mixture of alcohols, and the ammonium source is ammonia. In certain embodiments, the solvent is methanol, the ammonium source is ammonia, and the reaction mixture is heated to reflux at standard pressure (e.g., about 65° C.). In other embodiments, an ammonium salt is used, such as ammonium chloride.

In other embodiments, the process further comprises heating the solvent to about 30° C. or higher, about 40° C. or higher, to about 50° C. or higher, e.g., about 55° C. or higher, about 60° C. or higher, about 65° C. or higher, e.g., about 70° C. or higher, or e.g., heating the solvent to reflux.

In some embodiments, the solvent is a polar organic solvent. For example, the solvent is an alcohol, e.g., methanol, ethanol, or isopropanol. In other embodiments, the solvent is a polar protic solvent, such as an alcohol, or a mixture of alcohols. In other embodiments, the solvent is a polar aprotic solvent, such as dioxane.

The contemplated alkyl acetoacetate may be methyl acetoacetate. The contemplated alkyl acetoacetate may be ethyl acetoacetate.

In some embodiments, the ammonium source is a reagent that introduces —$NH_2$ group. In certain embodiments, the ammonium source is $NH_3$ or $NH_4Cl$. In some embodiments, the ammonium source provides $NH_4$+ to the reaction mixture, e.g., in the form of an ammonium salt or ammonia added to the reaction mixture. In some embodiments, the solvent is one in which the ammonium source is soluble, such as a C1-C4alkyl alcohol in combination with ammonia, such as methanol, or ethanol, or propanol, or butanol. Dioxane may also be used in certain embodiments.

In other embodiments, the methanesulfonyl agent is a reagent that introduces a methanesulfonyl group.

The methanesulfonyl agent may be methanesulfonyl chloride.

In certain embodiments, the base is a metal hydroxide, e.g., sodium hydroxide.

Also provided herein is a process of preparing a composition comprising a mixture of cis and trans isomers of a compound of Formula (X) having a majority of the cis isomer configuration, (X)

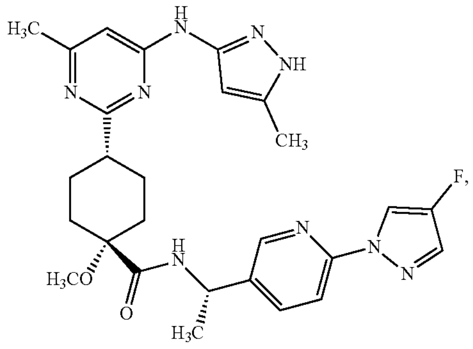

the process comprising:

reacting a compound of Formula (VII):

(VII)

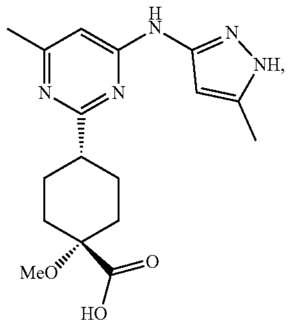

or a salt thereof, with a compound of Formula (VIII):

(VIII)

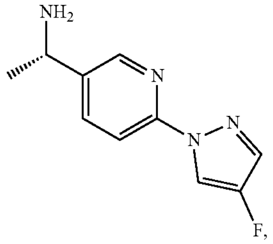

or a salt thereof, thereby providing the composition comprising a mixture of cis and trans isomers of the compound of Formula (X) having a majority of cis isomer configuration.

In some embodiments, the composition has a majority of cis isomer configuration has a cis:trans molar ratio of from about 4:1 to about 99:1, from about 5:1 to about 99:1, from about 6:1 to about 99:1, from about 7:1 to about 99:1, from about 8:1 to about 99:1.

In some embodiments, increasing the temperature at which the compound of Formula (II) is reacted with an ammonium source increases the molar ratio of cis:trans in the resulting mixture of compound of Formula (III) (i.e. a greater amount of the compound of Formula (IIIa) compared to Formula (IIIb)). In some embodiments, the ratio is about 4:1 to about 99:1, from about 5:1 to about 99:1, from about 6:1 to about 99:1, from about 7:1 to about 99:1, from about 8:1 to about 99:1. In some embodiments, performing the same reaction at room temperature (e.g., about 20° C.) produces a 1:1 ratio of cis:trans isomers, while heating the reaction to, e.g., reflux (such as between 60° C. to 70° C., or about 65° C.) produces a ratio of cis:trans isomers that is greater than 8:2. This increased cis:trans ratio can be carried through the next step of the synthetic route to produce a compound of Formula (IV), or pharmaceutically acceptable salt thereof, wherein there is a greater cis:trans ratio (i.e. a greater amount of the compound of Formula (IVa) compared to Formula (IVb)). In certain embodiments, the cis:trans ratio is about 4:1 to about 99:1, from about 5:1 to about 99:1, from about 6:1 to about 99:1, from about 7:1 to about 99:1, from about 8:1 to about 99:1 This is particularly advantageous because the cis isomer can be isolated and taken further on in the synthetic route to produce the desired compound of Formula (X), reducing the amount of trans compound of Formula (IV) (i.e., Formula (IVb)) that is discarded. Thus, in the methods provided herein, beating the reaction mixture comprising the compound of Formula (II) or salt thereof, ammonium source, and solvent, to a temperature of at least about 40° C., at least about 50° C., at least about 60° C., or at least about 70° C. (such as 50° C. to 80° C., or 60° C. to 70° C.) leads to an unexpected and advantageous shift of the cis:trans ratio in the resulting compound of Formula (III) or salt thereof (e.g., greater cis isomer than trans) that improves the efficiency of the synthesis of the compounds of Formula (IIIa), and (X), or salts thereof. In certain embodiments, the solvent used in the reaction of the compound of Formula (II) or salt thereof is a polar protic solvent or a polar aprotic solvent, or a mixture thereof. In some embodiments, the solvent comprises $C_1$-$C_4$alkyl alcohol or mixture of alcohols. In some embodiments, the solvent is methanol, or ethanol, or propanol, or butanol, or dioxane, or a combination thereof. In some embodiments the ammonium source is ammonia or ammonium chloride. In certain embodiments, the solvent is methanol and the ammonium source is ammonia. In some embodiments, the solvent is a $C_1$-$C_4$alkyl alcohol (such as methanol), the ammonium source is ammonia or ammonium chloride, and the solvent is heated to reflux (e.g., or 60° C. to 70° C., or higher depending on the solvent).

In other embodiments, the composition has a majority of cis isomer configuration has a cis:trans molar ratio of from about 97:3 to about 99:3, from about 9:1 to about 99:1, from about 9:1 to about 99:3, from about 9:1 to about 97:3, from about 95:5 to about 99:3, from about 95:5 to about 97:3, greater than or equal to about 9:1, greater than or equal to about 91:9, greater than or equal to about 92:8, greater than or equal to about 93:7, greater than or equal to about 94:6, greater than or equal to about 95:5, greater than or equal to about 96:4, greater than or equal to about 97 to 3, greater than or equal to about 99:3, greater than or equal to about 99:1, or for example, about a cis:trans isomer molar ratio of about 8:2 or more.

In certain embodiments, the process further comprises a process of preparing the compound of Formula (VII) or a salt thereof comprising:

(a) reacting a compound of Formula (IVa):

(IVa)

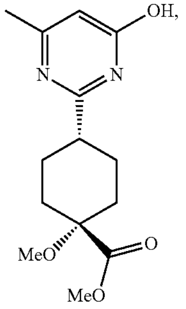

or a salt thereof with an activating agent, thereby providing a compound of Formula (V-1a):

(V-1a)

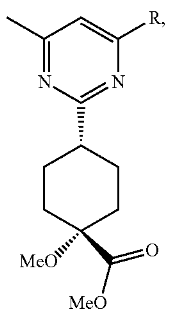

or a salt thereof, wherein R is an activating group;

(b) reacting the compound of Formula (V-1a) or a salt thereof with 5-methyl-3-pyrazolamine, thereby providing a compound of Formula (VI):

(VI)

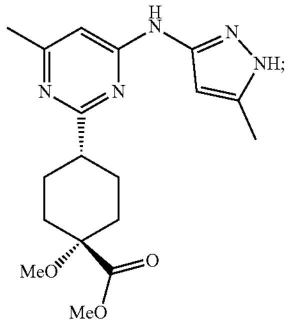

or a salt thereof;

(c) reacting the compound of Formula (VI) or a salt thereof with a base, thereby providing the compound of Formula (VII) or a salt thereof.

In certain embodiments, R is selected from the group consisting of —Cl, —O— methanesulfonyl, —O-p-toluenesulfonyl, a phosphite ester, chlorosulfite, and triflate. In some embodiments, R is —Cl or —OMs. In other embodiments, R is-OMs. In some embodiments, the activating agent is methanesulfonyl agent (e.g., MsCl).

Provided herein, in part, is a geometric isomeric mixture comprising a compound of Formula (X):

(X)

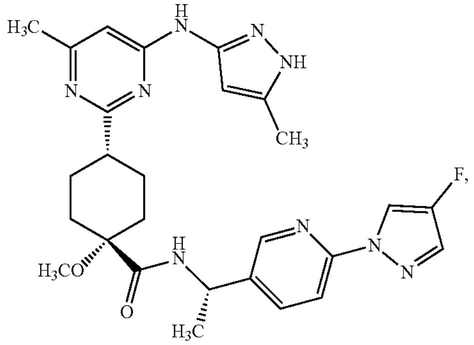

prepared with a disclosed process, wherein the geometric isomer mixture has a cis:trans molar ratio of from about 4:1 to about 99:1.

In some embodiments, the geometric isomer mixture has a cis:trans molar ratio of from about 4:1 to about 99:1, from about 5:1 to about 99:1, from about 6:1 to about 99:1, from about 7:1 to about 99:1, from about 8:1 to about 99:1.

In other embodiments, the geometric isomer mixture has a cis:trans molar ratio of from about 90:10 to about 99:1, greater than or equal to about 9:1, greater than or equal to about 91:9, greater than or equal to about 92:8, greater than or equal to about 93:7, greater than or equal to about 94:6, greater than or equal to about 95:5, greater than or equal to about 96:4, greater than or equal to about 97 to 3, greater than or equal to about 99:3, greater than or equal to about 99:1.

In certain embodiments, the geometric isomer mixture has a cis:trans molar ratio of from about 90:3 to about 99:3.

Pharmaceutical Compositions

Also provided herein is a pharmaceutical composition comprising pralsetinib or a pharmaceutically acceptable salt thereof and a pharmaceutically acceptable excipient or carrier. The term "pharmaceutically acceptable excipient" or "pharmaceutically acceptable carrier" refers to a pharmaceutically-acceptable material, composition or vehicle, such as a liquid or solid filler, diluent, excipient, solvent or encapsulating material, involved in carrying or transporting any subject composition or component thereof. Each excipient or carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutically acceptable excipient may be citric acid, hydroxypropyl methylcellulose (HPMC), magnesium stearate, microcrystalline cellulose (MCC), pregelatinized starch and sodium bicarbonate, a colorant (e.g., Brilliant Blue FCF), hypromellose, or titanium dioxide.

The compositions of the disclosure may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In some embodiments, the compositions of the disclosure are administered orally, intraperitoneally or intravenously. Sterile injectable forms of the compositions of this disclosure may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tween, Spans and other emulsifying agents or bioavailability enhancers which are commonly used in the manufacture of pharmaceutically acceptable solid, liquid, or other dosage forms may also be used for the purposes of formulation.

A composition for oral administration form can be prepared into any suitable dosage forms, such as capsule, dragee, granule, powder, or tablet. In a particular aspect, the dosage form is a capsule. In some embodiments, the size of the capsule is 0. In other embodiments, the size of the capsule is 00. In certain embodiments, the size of the capsule is 1.

In one aspect, the composition as described herein comprises about 10 mg, about 20 mg, about 30 mg, about 40 mg, about 50 mg, about 60 mg, about 70 mg, about 80 mg, about 90 mg, or about 100 mg of pralsetinib, or a pharmaceutically acceptable salt thereof. In one aspect, the composition as described herein comprises about 110 mg, 120 mg, 130 mg, 140 mg, 150 mg, 200 mg, 300 mg, or 400 mg of pralsetinib, or a pharmaceutically acceptable salt thereof.

The pharmaceutically acceptable compositions of this disclosure may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this disclosure may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this disclosure may also be administered topically, especially when the target of treatment includes areas or organs readily accessible by topical application, including diseases of the eye, the skin, or the lower intestinal tract. Suitable topical formulations are readily prepared for each of these areas or organs. Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this disclosure include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

The pharmaceutically acceptable compositions of this disclosure may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of the compounds of the present disclosure that may be combined with the carrier materials to produce a composition in a single dosage form will vary depending upon the host treated, the particular mode of administration.

Methods of Treatment

Pralsetinib or a compound of Formula (X) can be used in treating a RET-altered cancer. Accordingly, the present disclosure also provides methods of treating a RET-altered cancer comprising administering to a patient in need thereof a therapeutically effective amount of a composition disclosed herein. Another embodiment of the disclosure features a method of treating a patient with rearranged during transfection (RET)-positive locally advanced or metastatic non-small cell lung cancer (NSCLC) comprising administering to a patient in need thereof a therapeutically effective amount of a composition as disclosed herein. In a particular aspect, the (RET)-positive locally advanced or metastatic non-small cell lung cancer (NSCLC) is detected by an FDA approved test. Another embodiment of the disclosure features a method of treating a patient with RET-mutation positive locally advanced or metastatic medullary thyroid cancer (MTC) comprising administering to the patient in need thereof a therapeutically effective amount of a composition disclosed herein. In a particular aspect, the patient is 12 years of age or older. Another embodiment of the disclosure features a method of treating a patient with RET-fusion positive locally advanced or metastatic thyroid cancer who requires systemic therapy and has no satisfactory alternative treatment options, comprising administering to the patient in need thereof a therapeutically effective amount of a composition as disclosed herein. In a particular aspect, the patient is 12 years of age or older.

As used herein, the term "subject" or "patient" refers to an organism to be treated by a method of the present disclosure. Such organisms include, but are not limited to, mammals (e.g., murines, simians, equines, bovines, porcines, canines, felines, and the like), and in some embodiments, humans. In a particular aspect, the patient or subject is suffering from or suspected of suffering from a disease or disorder associated with aberrant RET expression (i.e., increased RET activity caused by signaling through RET) or biological activity. In particular, the disease or disorder is cancer. Many cancers have been linked to aberrant RET expression (Kato et al., Clin. Cancer Res. 23(8): 1988-97 (2017)). Non-limiting examples of "cancer" as used herein include lung cancer, head and neck cancer, gastrointestinal cancer, breast cancer, skin cancer, genitourinary tract cancer, gynecological cancer, hematological cancer, central nervous system (CNS) cancer, peripheral nervous system cancer, endometrial cancer, colorectal cancer, bone cancer, sarcoma, spitzoid neoplasm, adenosquamous carcinoma, pheochromocytoma (PCC), hepatocellular carcinoma, multiple endocrine neoplasia (MEN2A and MEN2B), and inflammatory myofibroblastic tumor. For other examples, see Nature Reviews Cancer 14: 173-86 (2014).

"Treat" and "treating" such a disease or disorder refers to ameliorating at least one symptom of the disease or disorder. These terms, when used in connection with a condition such as a cancer, refer to one or more of: impeding growth of the cancer, causing the cancer to shrink by weight or volume, extending the expected survival time of the patient, inhibiting tumor growth, reducing tumor mass, reducing size or number of metastatic lesions, inhibiting the development of new metastatic lesions, prolonging survival, prolonging progression-free survival, prolonging time to progression, and/or enhancing quality of life.

The term "therapeutic effect" refers to a beneficial local or systemic effect in animals, particularly mammals, and more particularly humans, caused by administration of a compound or composition of the disclosure. The phrase "therapeutically-effective amount" means that amount of a compound or composition of the disclosure that is effective to treat a disease or condition caused by over expression of RET or aberrant RET biological activity at a reasonable benefit/risk ratio. The therapeutically effective amount of such substance will vary depending upon the subject and disease condition being treated, the weight and age of the subject, the severity of the disease condition, the manner of administration and the like, which can readily be determined by one of skill in the art.

EXAMPLES

The following examples are intended to be illustrative and are not meant in any way to be limiting.

Compounds of the disclosure, including salts thereof, can be prepared using known organic synthesis techniques and can be synthesized according to any of numerous possible synthetic routes, such as those in the Synthetic Protocols below and in the Examples. The below Schemes are meant to provide general guidance in connection with preparing the compounds of the disclosure. One skilled in the art would understand that the preparations shown in the Schemes can be modified or optimized using general knowledge of organic chemistry to prepare various compounds of the disclosure.

Synthesis of methyl 4-cyano-1-methoxycyclohexane-1-carboxylate (Compound 3) Synthesis A

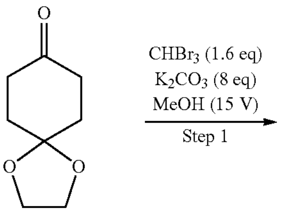

-continued

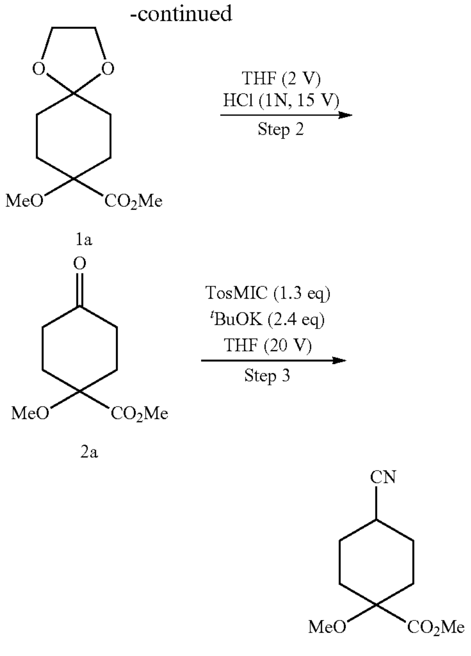

1a

2a

3

Synthesis A, Step 1. Synthesis of methyl 8-methoxy-1,4-dioxaspiro[4.5]decane-8-carboxylate (Compound 1a)

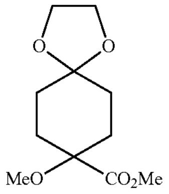

The reactor was charged with methanol (22.60 kg), and the internal temperature is set between 20~35° C. 1,4-dioxaspiro[4.5]decan-8-one (1.90 kg) and potassium carbonate (13.50 kg) were added into the reactor whilst maintaining the temperature range. Upon completion of the addition, the mixture was warmed to 35~40° C. Maintaining the temperature at 35~40° C., tribromomethane (4.94 kg) was added dropwise into the mixture at a rate of 2~4 kg/h. The mixture was stirred at 35~40° C. for the reaction. 4 h later, the reaction mixture was monitored by GC every 1~4 h until the area % of 1,4-dioxaspiro[4.5]decan-8-one is ≤1%. The reaction mixture was cooled to 20~30° C. The mixture was filtered with a filter funnel, and the filter cake was rinsed with methanol (3.04 kg). The filtrated was concentrated at T≤50° C. under reduced pressure (P≤−0.08 MPa) until 1~2 vol left. Maintaining the temperature at 20~35° C., ethyl acetate (8.60 kg), and purified water (15.20 kg) were added into the reactor. Maintaining the temperature at 15~30° C., the mixture was stirred for 15~30 min and settled for 15~30 min before separation. The organic phase was concentrated at T≤50° C. under reduced pressure (P≤−0.08 MPa) until 1~2 vol left. Obtained 2.86 kg light yellow oil in ~70% corrected yield with 92% GC purity.

➤ Analytical Method:

| | |
|---|---|
| Column: | HP-5, 30 m length × 0.32 mmID × 0.25 μm film |
| Carrier gas: | Helium gas |
| Flow rate | 1.9 ml/min |
| Run time | 22.5 min |
| Temp. program | 50° C. for 2 min; ramp at 20° C./min to 260° C., hold for 10 min |
| Inlet temp. | 250° C. |
| Detection temp. | 300° C. |

➤ Retention Times:

| Retention time, min | RRT | Chemical name | Area, % |
|---|---|---|---|
| 7.74 | 0.77 | Starting Material | 1% |
| 9.73 | 0.97 | Elimination impurity | 5% |
| 10.07 | 1.00 | Methyl 8-methoxy-1,4-dioxaspiro[4.5]decane-8-carboxylate | 92% |

Synthesis A, Step 2. Synthesis of methyl 1-methoxy-4-oxocyclohexane-1-carboxylate (Compound 2a)

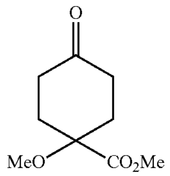 [SMILES: COC(=O)C1(OC)CCC(=O)CC1]

Maintaining the temperature at 10~25° C., Compound 1a (combined a batch (2.86 kg) including 1.96 kg of Compound 1a with another batch (2.62 kg) including 1.94 kg of Compound 1a) was added into the reactor and the stirrer was started. Maintaining the temperature at 10~25° C. 1M hydrochloric acid solution prepared of concentrated hydrochloric acid (4.60 kg) in purified water (43.12 kg) was added dropwise, the rate was according to the actual temperature. The mixture was stirred at 10~25° C. for reaction, 4 h later, the reaction mixture was monitored by GC every 2~6 h until the area % of Compound 1a was ≤5%. Maintaining the temperature at 10~25° C., dichloromethane (10.34 kg) was added into the mixture and the mixture was settled for 10~15 min before separation. The aqueous phase was extracted with dichloromethane (5.19 kg) at 10~25° C., the mixture was stirred for 10~30 min and settled for 10~15 min before separation. The organic phase was combined. The combined organic phase was concentrated at T≤40° C. under reduced pressure (P≤−0.08 MPa) until 1~2 vol left (relative to Compound 1a). Maintaining the temperature at 10~25° C., tetrahydrofuran (3.47 kg) was added into the reactor and the stirrer was started. Maintaining the temperature at 10~25° C. 1M hydrochloric acid solution prepared of concentrated hydrochloric acid (2.07 kg) in purified water (21.46 kg) was added dropwise, the rate was according to the actual temperature. The reaction mixture was reacted at 10~25° C., 4 h later, the reaction mixture was monitored by GC every 2~6 h until the area % of Compound 1a was ≤1.0%. Maintaining the temperature at 10~25° C., dichloromethane (10.34 kg) was added into the mixture and the mixture was settled for 10~15 min before separation. The aqueous phase was extracted with dichloromethane (5.19 kg) at 10~25° C., the mixture was stirred for 10~30 min and settled for 10~5 min before separation. The organic phase was combined. Anhydrous sodium sulfate (1.95 kg) was added into the organic phase and then the mixture was filtered with a 10 L filter flask. The filter cake was rinsed with dichloromethane (1.95 kg). The filter cake was sampled to analyze the purity by GC. The mixture was concentrated at T≤40° C. under reduced pressure (P≤−0.08 MPa) until 0.5~1 vol left (basically no distillate could be relative to Compound 2a). Obtained 3.40 kg (2.58 kg corrected) light brown oil in 81.98% yield with 97% GC purity.

➢ Analytical Method:

| | |
|---|---|
| Column: | HP-5, 30 m length × 0.32 mmID × 0.25 μm film |
| Carrier gas: | Helium gas |
| Flow rate | 1.9 ml/min |
| Run time | 22.5 min |
| Temp. program | 50° C. for 2 min; ramp at 20° C./min to 260° C., hold for 10 min |
| Inlet temp. | 250° C. |
| Detection temp. | 300° C. |

➢ Retention Times:

| Retention time, min | RRT | Chemical name | |
|---|---|---|---|
| 7.67 | 0.80 | Elimination impurity | 1.17 |
| 8.06 | 1.00 | Compound 2a | 97.16 |
| 9.44 | 1.16 | Compound 1a | 0.41 |

Synthesis A, Step 3. Synthesis of methyl 4-cyano-1-methoxycyclohexane-1-carboxylate (Compound 3)

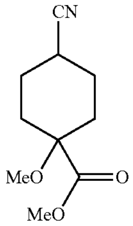

The reactor was charged with tetrahydrofuran (20.25 kg). Maintaining the temperature at 0~25° C., Compound 2a (1.97 kg, 1.50 kg corrected) was added into the reactor, followed by TosMIC (2.04 kg) and the stirrer was started. The mixture was cooled to −5~0° C. Maintaining the temperature at −5~0° C. a solution of potassium tert-butanolate (2.18 kg) in tert-butanol (7.26 kg) and tetrahydrofuran (3.45 kg) was added dropwise into the mixture and then adding rate was according to the temperature control. The mixture was allowed to react at −5~0° C. for 2 h and then warm to 5~10° C. 1 h later, the mixture was sampled for analysis every 1~3 h until area % of Compound 2a≤1% and 14.4 min (RRT=1.52) intermediate ≤1%. Maintaining the temperature at −5~15° C. a solution of sodium chloride (1.65 kg) in purified water (15.00 kg) was added into the mixture dropwise and the actual adding rate was according to the temperature control. The mixture was stirred for 10~15 min and settled for 10~15 min before separation. The aqueous phase was extracted with ethyl acetate (5.41 kg), the mixture was stirred for 10~15 min and settled for 10~15 min before separation. The aqueous phase was extracted with ethyl acetate twice (5.40 kg+2.70 kg), the mixture was stirred for 15~30 min and settled for 15~30 min before separation. The organic phase was combined. The organic phase was concentrated at T≤45° C. under reduced pressure (P≤−0.08 MPa) until 2~4 L left. Silica gel (0.75 kg) was added into the mixture and stirred to homogeneous through rotary evaporation, then the mixture was concentrated to dryness. The mixture was loaded into the preloaded column chromatographic and then sodium chloride (0.75 kg) was added on the surface and loaded flatly. Then the column chromatographic was eluted with a prepared solution of ethyl acetate (3.00 kg) in n-heptane (60.03 kg). The eluent was sampled for purity every 10 L until the entire product was washed. The mixture was concentrated at T≤45° C. under reduced pressure (P≤−0.08 MPa) until the solid precipitated out without obvious solvent left. The solid was transferred into trays and then was swept with nitrogen for drying. Obtained ~700 g white powder solid in ~50% corrected yield with 98~99% GC purity.

➢ Analytical Method:

| | |
|---|---|
| Column: | HP-5, 30 m length × 0.32 mmID × 0.25 μm film |
| Carrier gas: | Helium gas |
| Flow rate | 1.9 ml/min |
| Run time | 22.5 min |
| Temp. program | 50° C. for 2 min; ramp at 20° C./min to 260° C., hold for 10 min |
| Inlet temp. | 250° C. |
| Detection temp. | 300° C. |

➢ Retention Times:

| Retention time, min | RRT | Chemical name | |
|---|---|---|---|
| 8.08 | 0.85 | Elimination impurity | <0.05% |
| 8.68 | 0.91 | Compound 2a | <0.05% |
| 9.49 | 1.00 | Compound 3 (major) | 54.12 |
| 9.38 | 0.98 | Compound 3 (minor) | 43.35 |
| 14.27 | 1.52 | Intermediate | <0.05% |

The major and minor isomers of Compound 3 were the cis and trans isomers. However, the stereochemistry of the major and minor isomers was not assigned.

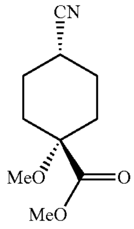

3 Cis

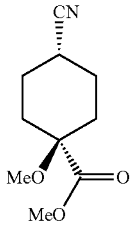

3 Trans

Synthesis of methyl 4-cyano-1-methoxycyclohexane-1-carboxylate (Compound 3) Synthesis B

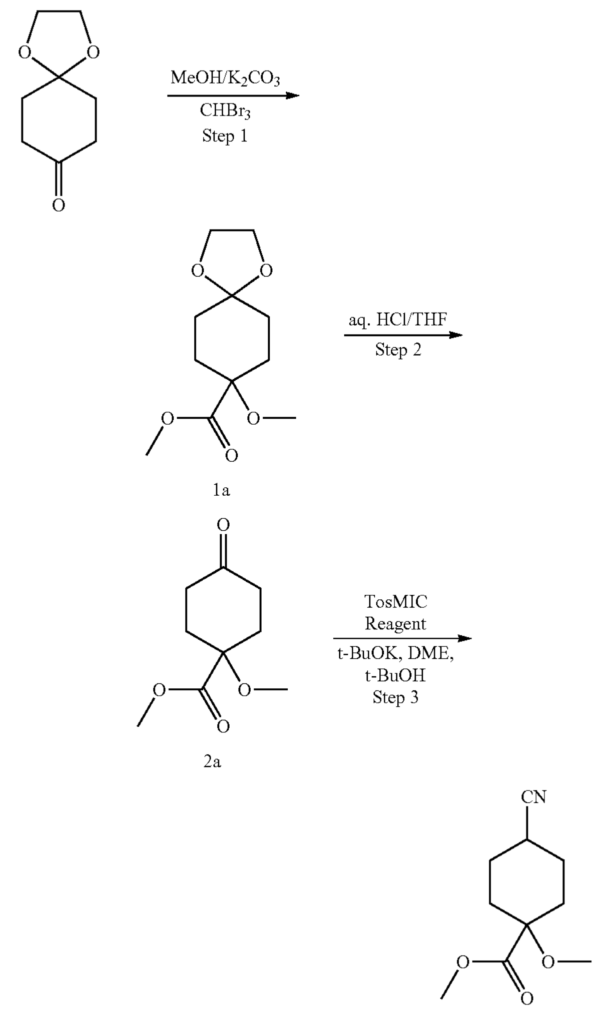

1a

2a

3

Synthesis B, Step 1. Synthesis of methyl 8-methoxy-1,4-dioxaspiro[4.5]decane-8-carboxylate (Compound 1a)

Methanol (15V) and $K_2CO_3$ (8 eq.) were taken in the vessel at 20° C. Cyclohexanedione monoethylene acetal (200.0 g, 1.0 eq) was added to the mixture. The slurry was then heated to 35-40° C. Bromoform (1.6 eq) was added to the reaction mass dropwise at 35-40° C. The reaction was maintained for 20 hrs or until the complete conversion of starting material at 35-40° C. After completion consumption of the cyclohexanedione monoethylene acetal, the reaction was filtered and concentrated to 2 vol. Water and ethyl acetate were added to the crude separated the organic layer. The organic layer was distilled to obtain the crude product as an oil. The yield of the crude: 76% with 92.07% purity (GC Method)

| Test | Content (%) |
|---|---|
| Bromoform | 1.00 |
| Cyclohexanedione monoethylene acetal | 0.22 |
| Compound 1a | 92.07 |
| Elimination impurity | 4.79 |
| Dimethoxy impurity | ND |

Synthesis B, Step 2. Synthesis of methyl 1-methoxy-4-oxocyclohexane-1-carboxylate (Compound 2a)

The crude Compound 1a (500 g) was treated with aq. HCl (1N 15V) in THF (2V) for 16 hrs or until the completion of starting material at 25-30° C. The reaction was extracted with DCM. The organic layer was distilled completely. Aq. HCl (1N 5V) was added followed by THF (1V) and maintained till completion of Compound 1a. The reaction was extracted with DCM. The organic layer was washed with 5% $NaHCO_3$, filtered, and concentrated to obtain the crude product. The yield of the crude: 71.7% with 94.90% purity (GC Method).

| Test | Content (%) |
|---|---|
| Bromoform | 1.06 |
| Compound 2a | 94.9 |
| Compound 1a | 0.32 |
| impurity | 2.39 |

Synthesis B, Step 3. Synthesis of methyl 4-cyano-1-methoxycyclohexane-1-carboxylate (Compound 3)

Compound 2a (100 g, 1.0 eq) was charged to dry RBF followed by TosMIC reagent (1.3 eq) and dimethoxyethane (18V) under nitrogen condition. Potassium tert butoxide (2.4 eq) was mixed t-butanol (6.25V) in another RBF to form a suspension/slurry. The slurry/suspension was added slowly to the reaction mass at −3-0° C. The reaction was maintained for 1-2 hr at 0° C. followed by 5 hrs at 25-30° C. After reaction completion, brine was added to the reaction mass and extracted with DME. The yield of the crude: 41%

Synthesis of methyl 4-cyano-1-methoxycyclohexane-1-carboxylate (Compound 3) Synthesis C

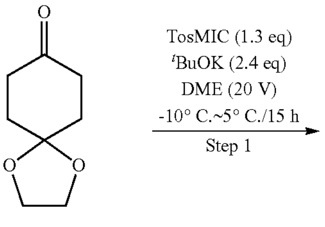

-continued

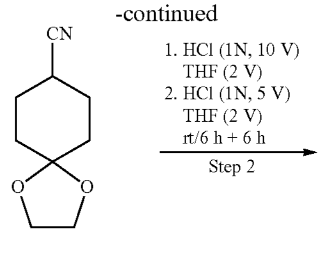

1b

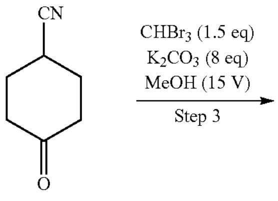

2b

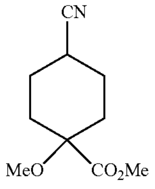

3

Synthesis C, Step 1. Synthesis of 1,4-Dioxaspiro[4.5]decane-8-carbonitrile (Compound 1b)

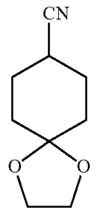

To a suspension of 1,4-dioxaspiro[4,5] decan-8-one (8.0 kg, 51.2 mol, 1.0 eq.) and p-toluenesulfonyl methyl isocyanide (13.0 kg, 66.6 mol, 1.3 eq.) in DME (150 L) was added a solution of potassium t-butoxide (13.6 kg, 121.2 mol, 2.4 eq.) in tBuOH (50 L) and DME (25 L) at −3-0° C. The reaction mixture was stirred for 1 h at 0° C., then 2 h at rt. The reaction mixture was allowed to warm to room temperature and stirred for 5 h. Brine (100 kg) was added and extracted with DME (25 L). The combined organic phase was concentrated under reduced pressure. The residue was distilled (100~120° C., 5 mm Hg) to give compound 1 (5.6 kg, 66%) as an oil.

Synthesis C, Step 2. Synthesis of 4-oxocyclohexane-1-carbonitrile (2b)

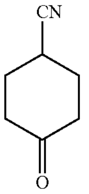

4-oxocyclohexane-1-carbonitrile

To a solution of Compound 1b (3.0 kg, 17.9 mol) in THF (6 L, 2 V) was added HCl (1 N, 10 V) at room temperature. The reaction mixture was stirred at r.t. overnight. The reaction solution was extracted with DCM (3x3 L). All the crude Compound 2b (contained some Compound 1b) was concentrated and then treated with HCl (1 N, 5 V) and THF (3 L, 1 V) again. The resulting mixture was stirred at room temperature for 4 h, and extracted with DCM (3x3 L). The combined organic phases were washed with 5% $NaHCO_3$ (5 L) and dried over anhydrate $Na_2SO_4$, filtered and concentrated under reduced pressure to give Compound 2b (1.7 kg, 78%) as a yellow oil.

Synthesis C, Step 3. Methyl 4-cyano-1-methoxycyclohexanecarboxylate (3)

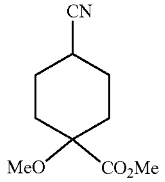 [SMILES: COC(=O)C1(OC)CCC(C#N)CC1]

To a solution of compound 2b (1.5 kg, 12.2 mol, 1.0 eq.) and $CHBr_3$ (4.6 kg, 36.6 mol, 1.5 eq.) in MeOH (22.5 L, 15 V) was added $K_2CO_3$ (13.5 kg, 97.6 mol, 8.0 eq.) in portions at 0° C. The reaction mixture was stirred for 3 h at 0° C. then 3d at room temperature. The salt was filtered off and the filtrate was concentrated under reduced pressure. The residue was dissolved in water (12 L, 8 V) and extracted with EtOAc (7.5 Lx3). The combined organic phases were dried over anhydrate $Na_2SO_4$, filtered and concentrated under reduced pressure to give crude Compound 3 (2.0 kg, 74% yield) as a solid. The mass spectrum was analyzed by mass spectrometry with atmospheric pressure chemical ionization (APCI) in positive ion mode and shows the measured mass (m/z) 198.1121 is consistent with the theoretical $[M+H]^+$ mass of (m/z) 198.1125.

| $^1H$ Data (Major Isomer) | $^{13}C$ Data (Major Isomer) | $^1H$ Data (Minor Isomer) | $^{13}C$ Data (Minor Isomer) |
|---|---|---|---|
| — | 122.01 | — | 121.66 |
| 2.58-2.42 (m, 0.6H) | 27.16 | 2.92-2.81 (m, 0.4H) | 26.37 |
| 1.99-1.42 (m, 2.4H) | 24.52 | 1.99-1.42 (m, 1.6H) | 23.68 |
| 2.16-2.00 (m, 1.2H); 1.99-1.42 (m, 1.2H) | 30.01 | 2.16-2.00 (m, 0.8H); 1.99-1.42 (m, 0.8H) | 28.13 |
| — | 77.97 | — | 77.54 |

-continued

| $^{1}H$ Data (Major Isomer) | $^{13}C$ Data (Major Isomer) | $^{1}H$ Data (Minor Isomer) | $^{13}C$ Data (Minor Isomer) |
|---|---|---|---|
| 3.24 (s, 1.7H) | 51.84 | 3.22 (s, 1.3H) | 51.84 |
| — | 173.80 | — | 173.42 |
| 3.75 (s, 1.7H) | 52.33 | 3.77 (s, 1.3H) | 52.31 |

Synthesis of methyl 4-(imino(methoxy)methyl)-1-methoxycyclohexane-1-carboxylate hydrochloride (Compound 4)

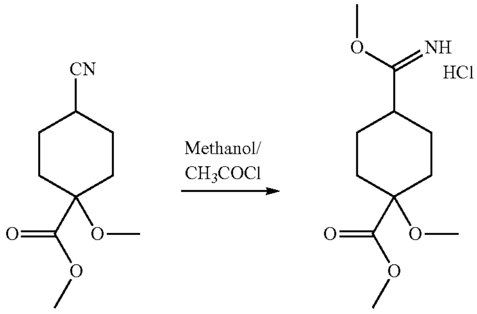

3 4

Synthesis A

Compound 3 (50 g, 1.0 eq) was taken in dry round bottom flask (RBF) and added methanol (5V). Acetyl chloride (5V) was added dropwise to the RBF at 0-5° C. The reaction was maintained until the consumption of the starting material. To the reaction mixture was added diisopropyl ether and stirred for 1 h. The suspension was filtered and dried to obtain Compound 4. Compound 4 was taken on to the next step without further purification.

Alternatively. Compound 3 may be dissolved in a solvent or solvent mixture (e.g., isopropyl ether, methanol), and HCl gas can be bubbled through the solvent to generate Compound 4.

Synthesis B

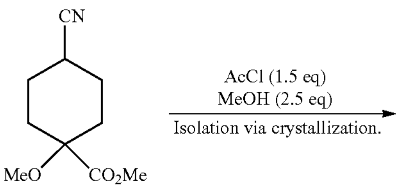

3

-continued

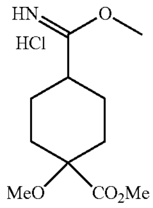

4

To a solution of Compound 3 (2.0 kg, 10.1 mol, 1.0 eq.) in MeOH (810 g, 25.3 mol, 2.5 eq.) was added AcCl (1.2 kg, 15.2 mol, 1.5 eq.) dropwise under 0° C. The reaction mixture was stirred at room temperature for 2d. Then $iPr_2O$ (6 L) was added and stirred 1 h. The solid was collected by filtration to give Compound 4 (~2.4 kg) as a solid.

Synthesis C

The reactor was charged with methanol (1.109 kg, 4 vol). Maintaining the temperature at 0~25° C., Compound 3 (0.352 kg, 1.0 eq.) was added into the reactor and the reactor was stirred. The mixture was cooled to −5~0° C. in an ice-bath. Maintaining the temperature at 0~5° C., acetyl chloride (0.838 kg, 6.0 eq) was added dropwise into the mixture, and then the adding rate was according to the temperature control. The mixture was warm to RT slowly in agitating. 10 h later, the mixture was sampled for analysis every 1~3 h until area % of Compound 3≤1%. The mixture was concentrated to ~1 vol at T≤30° C. under reduced pressure (P≤−0.08 MPa). Then, exchange methanol with 3*2 vol methyl tert-butyl ether (MTBE). To the mixture was added 2 vol MTBE and agitating at 0~5° C. for 2 h. The mixture was filtered the mixture and the wet cake rinse with 1 vol pro-cooling MTBE. The solid was transferred into trays and then was swept with nitrogen for drying. 12 h later. ~315 g off-white powder solid in ~68% crude yield with 96% GC purity.

Compound 4 was analyzed by mass spectrometry with atmospheric pressure chemical ionization (APCI) in positive ion mode. The mass spectrum showed the measured mass (m/z) 230.1393, consistent with the theoretical $[M+H]^+$ mass of (m/z) 230.1387.

➤ Analytical Method:

| | |
|---|---|
| Column: | HP-5, 30 m length × 0.32 mmID × 0.25 μm film |
| Carrier gas: | Helium gas |
| Flow rate | 1.9 ml/min |
| Run time | 22.5 min |
| Temp. program | 50° C. for 2 min; ramp at 20° C./min to 260° C., hold for 10 min |
| Inlet temp. | 250° C. |
| Detection temp. | 300° C. |

| $^{1}H$ Data[a] (Major Isomer) | $^{13}C$ Data[b] (Major Isomer) | $^{1}H$ Data[a] (Minor Isomer) | $^{13}C$ Data[b] (Minor Isomer) |
|---|---|---|---|
| — | 173.98 | — | 172.71 |
| 2.40-2.29 (m, 0.7 H) | 40.99 | 3.08-3.02 (m, 0.3 H) | 40.34 |
| 1.96-1.39 (m, 2.8 H) | 23.44 | 1.96-1.39 (m, 1.2 H) | 25.47 |
| 2.18-1.97 (m, 1.4 H); 1.96-1.39 (m, 1.4 H) | 29.96 | 2.18-1.97 (m, 0.6 H); 1.96-1.39 (m, 0.6 H) | 31.03 |
| — | 78.83 | — | 77.37 |

-continued

| $^{1}H$ Data[a] (Major Isomer) | $^{13}C$ Data[b] (Major Isomer) | $^{1}H$ Data[a] (Minor Isomer) | $^{13}C$ Data[b] (Minor Isomer) |
|---|---|---|---|
| 3.25 (s, 2.0 H) | 51.94 | 3.22 (s, 1.0 H) | 51.88 |
| — | 182.26 | — | 182.29 |
| 3.74 (s, 2.0 H) | 52.36 | 3.80 (s, 1.0 H) | 52.43 |
| 4.31 (s, 2.1 H) | 60.98 | 4.31 (s, 0.9 H) | 61.11 |
| 12.47 (s, 0.7 H); 11.66 (s, 0.7 H) | — | 12.47 (s, 0.3 H); 11.66 (s, 0.3 H) | — |

Synthesis of methyl 4-carbamimidoyl-1-methoxycyclohexane-1-carboxylate (Compound 5) and methyl 4-(4-hydroxy-6-methylpyrimidin-2-yl)-1-methoxycyclohexane-1-carboxylate (Compound 6)

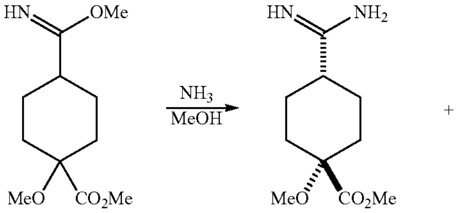

4

5 (Cis isomer)

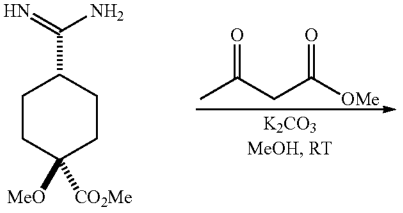

5 (Trans isomer)

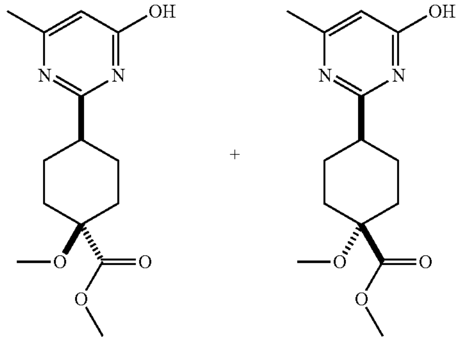

6 (cis isomer)

6 (trans isomer)

| Effect of Temperature for 4 --> 5 | | |
|---|---|---|
| | 0° C. to RT | d.e. 1:1 cis:trans Compound 5<br>d.e. 1:1 cis:trans Compound 6 |
| | 0° C. to reflux | d.e. >8:2 cis:trans Compound 5<br>d.e. >8:2 cis:trans Compound 6 |

Compound 5, Synthesis A

Compound 4 (from 135 g starting material of compound 3) was taken in a dry RBF and added methanol (2V). The mixture was cooled to 0-5° C. and added methanolic ammonia (10V). The reaction was maintained until completion consumption of Compound 4 at 25-30° C. Heating allowed for cis:trans isomerization to progress further toward the cis-Compound 5. The reaction mass was distilled completely and swapped twice with methanol to afford off white color solid (~2:1 cis:trans).

Compound 5, Synthesis B

The reactor was charged with 7N $NH_3$/MeOH (1.48 kg, 10. eq) at 0-25 C. While maintaining the temperature at 0-25° C., Compound 4 (0.35 kg, crude) was added into the reactor. The mixture was warmed to 20-30° C. slowly in agitating. After 10 h, the mixture was sampled for analysis every 1~3 h until area % of Compound 4≤5%. The mixture was warmed to 55~60° C. for 1~2 h and sampled to monitor the ratio of cis:trans. The typical ratio for cis:trans was 80:20~85:15. The mixture was concentrated to ~1 vol at T≤30° C. under reduced pressure (P≤−0.08 MPa). Then, a solvent exchange of methanol with 3*2 vol Heptane was performed. An additional 2 vol heptane was added to the mixture and stirring continued at 0~5° C. for 2 h. The mixture was filtered and the wet cake rinses with 1 vol pre-cooled heptane. The solid was transferred into trays and was swept with nitrogen for drying. Obtained off-white powder solid in ~100% crude yield with 92% HPLC-CAD purity.

➢ Analytical Method:

| | |
|---|---|
| Column: | Atlantis T3, 4.6 * 150 mm, 3.0 um |
| Column Temperature: | 40° C. |
| Flow rate | 1.0 ml/min |
| Injection Volume | 5 ul |
| Mobile Phase | A: 0.1% FA in water<br>B: 0.1% FA in ACN |
| Gradient Table | T(min) 0.0 9.0 12.0 12.1 18.0<br>B % 0 95 95 0 0 |
| CAD Detection | Data Collection Rate: 10 Hz<br>Filter: 1.0 |
| Run time | 18.0 min |

The ratio of cis:trans: HPLC-UV

| | |
|---|---|
| Column: | Atlantis T3. 4.6 * 150 mm, 3.0 um |
| Column Temperature: | 20° C. |
| Flow rate | 1.0 ml/min |
| Injection Volume | 5 ul |
| Mobile Phase | A: 0.1% FA in water<br>B: 0.1% FA in ACN |
| Gradient Table | T(min) 0.0 9.0 12.0 12.1 18.0<br>B % 0 95 95 0 0 |
| Detection | 210 nm |
| Run time | 18.0 min |

Compound 6, Synthesis A

The reactor was charged with methanol (1.14 kg, 4 vol) and Compound 5 (360 g, 1.0 eq). The reactor was charged with methyl acetoacetate (0.21 kg, 1.1 eq) and $K_2CO_3$ (0.81 kg, 3.5 eq) at RT. The mass heated to 65~68° C. quickly. 1~2 h later, the mixture was sampled for analysis every 0.5~1 h until area % of Compound 5≤2%. The mixture was cooled down to RT rapidly after IPC complete. The reaction mixture was filtered, the wet cake was washed with 2 vol MeOH and 2 vol DCM. The filtrates and the rinse solvents were combined. The combined organics were evaporated to 0.5~1 vol below T≤45° C. under vacuum (P≤−0.08 MPa) and then $H_2O$ (5V) was added to the dilute the mixture. The solution was adjusted to pH=5 by HCl (2 N), then added 5 vol DCM to dissolve. The mixture was allowed to settle 10~15 min and the layers were separated. The aqueous phase was extracted with 2 vol DCM. The organics were combined and then washed with an 8 vol saturated $NaHCO_3$ solution. The phases were separated. The organic layer was washed with 8 vol water, and the layers were separated. The organic layer was concentrated to 1~2 vol at T≤50° C. under reduced pressure (P≤−0.08 MPa). Then, a solvent exchange from DCM to EtOAc occurred with 2*4 vol EA. To the mixture was added 4 vol EA. The mixture was heated to 55~60° C. and held for 2 h. The mixture was cooled to 0~5° C. and stirring for 2 h. The mixture was filtered and dried to provide Compound 6. This yielded 250 g of Compound 6 as a white solid. 250 g off-white crude was obtained with 99% purity and cis:trans=75:25. The reactor was charged with crude Compound 6 and 10 vol EA (base on crude weight). The mixture was heated to 55~60° C. and agitated for 2 h. The mixture was cooled down to 0~5° C. for 2 h. The mixture was filtered and washed with pre-cooled EA. The cake dried in a vacuum at 45~50° C. until KF≤0.5% and EA residue ≤0.2%. Obtained ~152 g white powder solid in ~32% corrected yield (over 3 steps) with 100% purity by HPLC. The ratio of the product was 97:3 cis:trans by releasing method.

➤ Analytical Method:

IPC: HPLC-CAD

| | |
|---|---|
| Column: | Atlantis T3, 4.6 * 150 mm, 3.0 um |
| Column Temperature: | 40° C. |
| Flow rate | 1.0 ml/min |
| Injection Volume | 5 ul |
| Mobile Phase | A: 0.1% FA in water<br>B: 0.1% FA in ACN |
| Gradient Table | T(min) 0.0 9.0 12.0 12.1 18.0<br>B % 0 95 95 0 0 |
| CAD Detection | Data Collection Rate: 10 Hz<br>Filter: 1.0 |
| Run time | 18.0 min |

Releasing Method:

| | |
|---|---|
| Column: | YMC-Pack pro-C18, 3 um particle size, 4.6 mm * 150 mm |
| Column Temperature: | 30° C. |
| Flow rate | 1.0 ml/min |
| Injection Volume | 5 ul |
| Mobile Phase | A: 100% ACN<br>B: 100% water |
| Gradient Table | T(min) 0 25 30<br>B % 95 15 95<br>A % 5 85 95 |
| Detection | 235 nm |
| Run time | 30 min |

Compound 6, Synthesis B

To a solution of Compound 5 (9.0 mol) in MeOH (~7.4 L) were added methyl 3-oxobutanoate (1.1 kg, 9.9 mol, 1.1 eq.) and NaOMe/MeOH (30%, 3.6 L) and the reaction mixture was reflux overnight. The solvent was removed under reduced pressure and the residue was diluted with water (12 L, 5 V). The solution was adjusted to pH=5 by HCl (2 N) and the solid was collected by filtration then dissolved in DCM (12 L) and washed with $NaHCO_3$ (sat.) (16 L) and $H_2O$ (16 L), separated, the organic was dried over anhydrate $Na_2SO_4$, filtered and concentrated under reduced pressure to give Compound 6 (>95:5 cis:trans). Triturated from EtOAc (800 mL) to give Compound 6 (710 g, 20.8% over 4 steps) as a white solid. $^1H$ NMR (400 MHz, $CDCl_3$): δ 12.78 (s, or 1H), 6.16 (s, 1H), 3.77 (s, 3H), 3.30 (s, 3H), 2.64-2.67 (m, 1H), 2.31 (s, 3H), 2.14-2.18 (m, 2H), 1.80-1.98 (m, 6H).

Compound 6 (theoretical m/z 280.1423) was analyzed by mass spectrometry with electrospray ionization (ESI), in positive ion mode. ESI-MS shows the main measured mass (m/z) 281.1504 consistent with the Compound 6 form $[M+H]^+$ (m/z) 281.1496. The measured mass (m/z) 344.1609 was consistent with $[M+H_2O+2Na]^+$ (m/z) 344.1319.

| $^1H$ Data | $^{13}C$ Data |
|---|---|
| 12.15 (s, 1H) | — |
| — | 162.54 |
| 5.99 (s, 1H) | 110.03 |
| — | 164.23 |
| 2.14 (s, 3H) | 23.42 |
| — | 185.04 |
| 2.60-2.51 (m, 1H) | 41.16 |
| 1.82-1.52 (m, 4H) | 24.59 |
| 2.02 (dt, J = 11.2, 2.5 Hz, 2H); 1.82-1.52 (m, 2H) | 30.26 |
| — | 77.48 |
| 3.13 (s, 3H) | 51.16 |
| — | 173.98 |
| 3.67 (s, 3H) | 51.85 |

Synthesis of methyl (1s,4s)-1-methoxy-4-(4-methyl-6-((methylsulfonyl)oxy)pyrimidin-2-yl)cyclohexane-1-carboxylate (Compound 7)

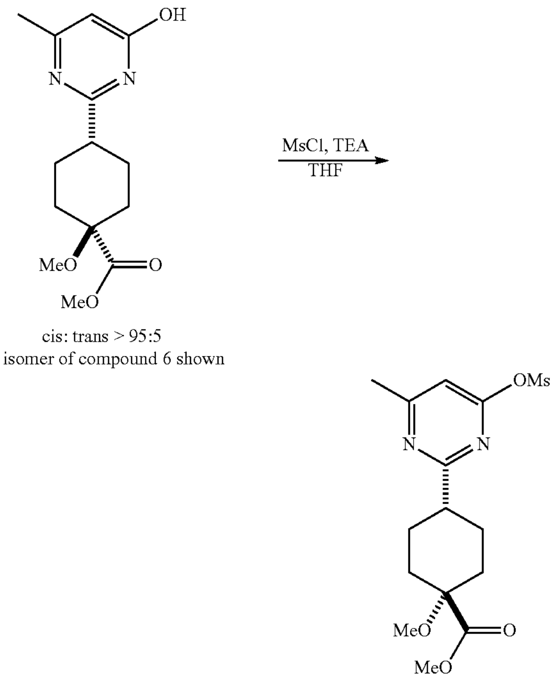

cis: trans > 95:5
cis isomer of compound 6 shown

7

Compound 7 intermediate was prepared by reaction of Compound 6 (1.00 Kg±1%) with methanesulfonyl chloride (0.31 L±1%, 1.1 equivalents) and triethylamine (0.60 L±1%, 1.2 equivalents) in tetrahydrofuran (4.50 L±5%) at a temperature between 0° C. and 10° C. to give Compound 7 non-isolated intermediate (>97:3 cis:trans). This immediate was carried to the next reaction with no purification.

Compound 7 (theoretical m/z 358.1199) was analyzed by mass spectrometry with electrospray ionization (ESI), in positive ion mode. ESI-MS showed the main measured mass (m/z) 359.1284 consistent with the Compound 7 form $[M+H]^+$ (m/z) 359.1271. The measured mass (m/z) 381.1136 was consistent with $[M+Na]^+$ (m/z) 381.1096. The measured mass (m/z) 344.1595 was consistent with $[M+H—CH_3]^+$ (m/z) 344.1042. The measured mass (m/z) 281.1505 was consistent with $[M-SO_3CH_3+H_2O]^+$ (m/z) 281.1496.

| $^1$H Data | $^{13}$C Data |
|---|---|
| 3.58 (s, 3H) | 41.83 |
| — | 164.63 |
| 6.78 (s, 1H) | 107.93 |
| — | 171.33 |
| 2.56 (s, 3H) | 24.31 |
| — | 173.77 |
| 2.93 (tt, J = 10.4, 5.1 Hz, 1H) | 45.42 |
| 2.11-1.97 (m, 1H); 1.97-1.83 (m, 3H) | 25.88 |
| 2.22-2.11 (m, 2H); 1.97-1.83 (m, 1H); 1.83-1.76 (m, 1H) | 31.05 |
| — | 78.42 |
| 3.27 (s, 3H) | 51.88 |
| — | 174.95 |
| 3.77 (s, 3H) | 52.23 |

Synthesis of methyl (1s,4s)-1-methoxy-4-(4-methyl-6-((5-methyl-1H-pyrazol-3-yl)amino)pyrimidin-2-yl) cyclohexane-1-carboxylate (Compound 8)

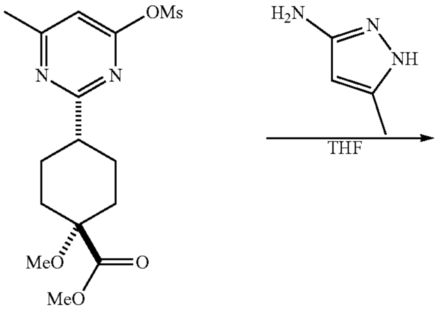

7

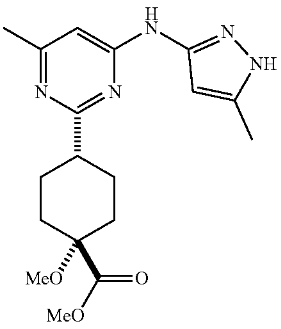

8

To the reaction mixture was then added 5-methyl-3-pyrazolamine (0.52 Kg±1%, 1.5 equivalents), followed by a tetrahydrofuran (1.00 L±5%) rinse, and the reaction mixture was heated to reflux temperature to form Compound 8 non-isolated intermediate. This intermediate was taken forward with no further purification. Cis:trans ratio was the same as the input material Compound 6 with a ratio of >97:3 cis:trans.

5-methyl-3-pyrazolamine can be synthesized from 3-aminocrotononitrile, hydrazine, and water by methods like those disclosed in CN107980784, WO2014147640, U.S. Pat. No. 808,066, CN104844567, and CN108341782.

Compound 8 (theoretical m/z 359.1957) was analyzed by mass spectrometry with electrospray ionization (ESI), in positive ion mode. ESI-MS showed the main measured mass (m/z) 360.2035 consistent with the Compound 8 form $[M+H]^+$ (m/z) 360.2030.

| $^1$H Data | $^{13}$C Data |
|---|---|
| 2.31 (s, 3H) | 11.75 |
| — | 138.17 |
| 9.96 (s, 1H) | — |
| — | 148.09 |
| 6.08 (s, 1H) | 95.62 |
| 7.46 (s, 1H) | — |
| — | 160.06 |
| 6.70 (s, 1H) | 101.82 |
| — | 166.32 |
| 2.36 (s, 3H) | 24.33 |
| — | 172.84 |
| 2.75 (tt, J = 10.9, 4.5 Hz, 1H) | 46.09 |
| 2.07-1.97 (m, 1H); 1.97-1.78 (m, 3H) | 26.16 |
| 2.22-2.09 (m, 2H); 1.97-1.78 (m, 1H); 1.78-1.72 (m, 1H) | 31.33 |
| — | 78.78 |
| 3.29 (s, 3H) | 51.90 |
| — | 175.34 |
| 3.76 (s, 3H) | 52.21 |

Synthesis of (1s,4s)-1-methoxy-4-(4-methyl-6-((5-methyl-1H-pyrazol-3-yl)amino)pyrimidin-2-yl)cyclohexane-1-carboxylic acid (Compound 9)

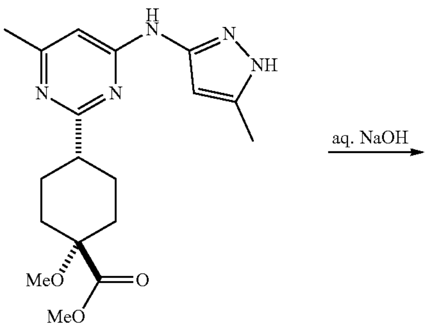

8

-continued

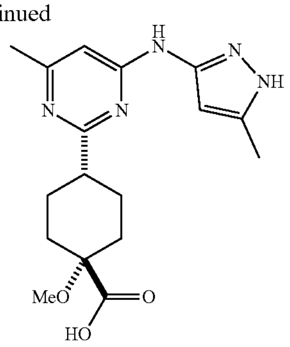

9

Upon reaction completion of Compound 8, the reaction mixture was cooled to a temperature between 30° C. and 25° C. and a previously prepared solution of deionized water (9.00 L±5%) and sodium hydroxide 50% w/w (1.34 Kg±1%, 4.7 equivalents) was charged to the reaction mixture to form Compound 9. The reaction mixture was stirred at a temperature between 30° C. and 25° C. until reaction completion and tetrahydrofuran (5.50 L±5%) was charged at a rate of not more than 4.44 Kg/(h·Kg), while maintaining the temperature between 30° C. and 25° C. The suspension was cooled to a temperature between 25° C. and 15° C. with a cooling rate of not more than 6° C./h. The suspension was stirred for not less than 4 hours and not more than 10 hours at a temperature between 15° C. and 25° C. The suspension was filtered, and the wet cake was washed with deionized water (2.00 L±5%) at a temperature between 15° C. and 25° C., and twice with acetone (2.00 L±5%) at the same temperature. The wet solid was dried under a vacuum at a temperature not more than 40° C. until the content of water by KF was lower or equal to 17% w/w and the content of triethylamine was lower than 5000 ppm by GC. Yield 65-85% over the 3 steps.

Compound 9 (theoretical m/z 345.1801) was analyzed by mass spectrometry with electrospray ionization (ESI), in positive ion mode. ESI-MS showed the main measured mass (m/z) 346.1876 consistent with the Compound 9 form $[M+H]^+$ (m/z) 346.1874. The gas-phase ion observed at 208.0395 m/z was consistent with cleavage at the pyrimidine ring, resulting in the proposed protonated fragment and water (m/z) 208.1193.

| $^1H$ Data | $^{13}C$ Data |
|---|---|
| 2.20 (s, 3H) | 10.79 |
| — | 138.50 |
| 12.23 (or s, 1H) | — |
| — | 148.37 |
| 6.16 (s, 1H) | 95.28 |
| 9.52 (s, 1H) | — |
| — | 159.82 |
| 6.86 (s, 1H) | 101.61 |
| — | 164.51 |
| 2.24 (s, 3H) | 23.76 |
| — | 171.92 |
| 2.61 (tt, J = 11.3, 3.8 Hz, 1H) | 45.40 |
| 1.91-1.77 (m, 2H); 1.77-1.67 (m, 2H) | 25.81 |
| 2.06-1.91 (m, 2H); 1.77-1.67 (m, 1H); 1.67-1.61 (m, 1H) | 30.56 |
| — | 77.47 |
| 3.18 (s, 3H) | 50.95 |
| — | 175.56 |
| 12.23 (br s, 1H) | — |

Synthesis of 4-fluoro-1H-pyrazole hydrochloride (Compound 16) Synthesis A

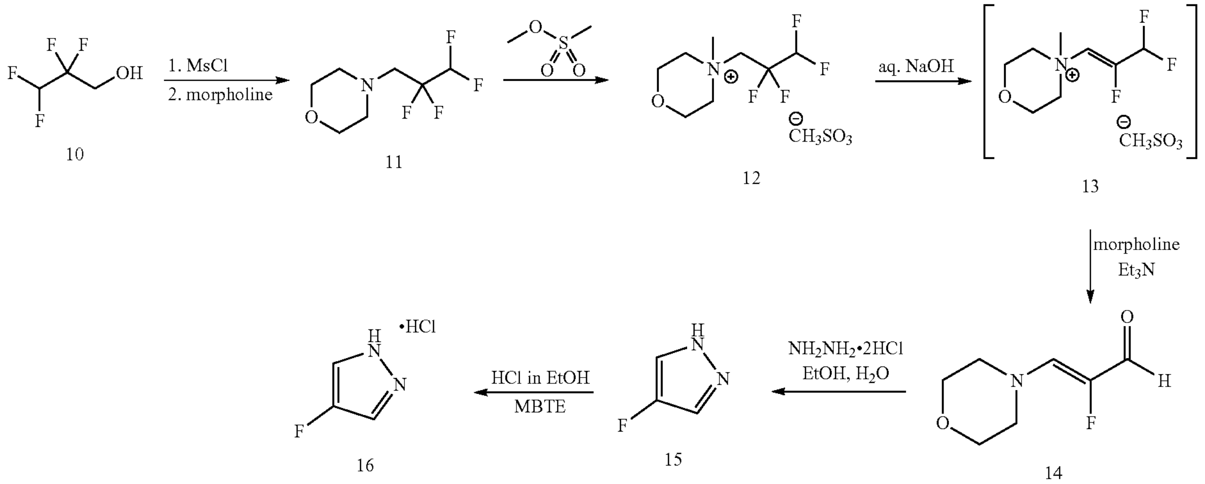

Synthesis of Compound 11: A mixture of 10 (200 g, 1.0 equiv.), methane sulfonyl chloride (1.1 equiv.) in ethyl acetate (3.0 rel. volumes) was cooled to 0-5° C. before triethylamine (1.2 equiv.) was added between 0-20° C. After the addition was finished the reaction mixture was stirred at 20-30° C. until the reaction was complete. To the resulting mixture was added water (3.0 rel. volumes) and the phases were split. Subsequently, the aqueous layer was extracted with ethyl acetate (1.0 rel. volume), then the combined organic layers were washed with water (2.0 rel. volumes) before being concentrated in vacuo at 40-45° C. This generated pure compound 11 when considering EtOAc content (94.9% area with 4.8% area EtOAc) in excellent yield (93%). A mixture of compound 11 (294 g, 1.0 equiv.) and morpholine (4.0 equiv.) was heated to 130-135° C. until the reaction was complete. The resulting mixture was cooled to 90° C., whereupon water (1.0 rel. volume) was added. The reaction mass was further cooled to 20-30° C. and the phases were split. The resulting aqueous layer was extracted with ethyl acetate (2×1.0 rel. volume). The organic layers were combined and washed with water (2×1.0 rel. volumes) before being concentrated in vacuo at 40-45° C. This yielded pure 2 when considering EtOAc content (94.8% area with 4.7% area EtOAc) in excellent yield (91%).

Synthesis of Compound 12: Methyl methanesulfonate (1.1 equiv.) was heated to 130-135° C. before 11 (1.71 kg, 1.0 equiv) was added dropwise. After the addition was finished the reaction mixture was cooled to 100-105° C. and stirred at this temperature until the reaction was complete. Subsequently, the reaction mixture was cooled to approx. 85° C. and isopropyl alcohol (IPA) (1.5 rel. volumes) was added. The mass was then allowed to cool to 0-5° C. and stirred for 30 min. The resulting precipitate was filtered, and the solid was washed with IPA (0.5 rel. volumes) before being dried in vacuo at 45-50° C. A total of 2.34 kg (88%) off-white solid was obtained.

Synthesis of Compound 13 and 14: A solution of 12 (1.0 equiv) dissolved in water (1.0 rel. volume) was heated to 50-60° C., whereupon sodium hydroxide (10 M, 1.15 equiv) was added. Then the mass was stirred at this temperature until the reaction was complete. Subsequently, the mass was cooled to 20-30° C. and filtered through Celite. The Celite pad was washed with water (0.2 rel. volumes), and the resulting aqueous solution was directly added to a mixture of morpholine (1.0 equiv) and TEA (2.0 equiv) that was heated at 70-80° C. This mixture was then stirred at this temperature until the reaction was complete. Subsequently, the reaction mixture was cooled to 20-30° C. and diluted with DCM (2.0 rel. volumes). The phases were separated, and the aqueous layer was extracted with DCM (2×2.0 rel. volumes). The combined organic layers were washed with a solution of saturated potassium carbonate (1.0 rel. volume) then concentrated in vacuo at 40-45° C. Afterward, toluene (2.0 rel. volumes) was added and the distillation recommenced removing 1.0 rel. the volume of toluene. The resulting slurry was cooled to 0-5° C. and filtered. The solid was washed with toluene (0.2 rel. volumes) and dried in vacuo at 45-50° C. A total of 1.28 kg (78%) brown solid is obtained. HPLC purity: 98.3% area. GC purity: 99.4% area at RT 21.4 min.

Synthesis of Compound 15: To (Z)-2-fluoro-3-morpholino-prop-2-enal (Compound 14, 1.2 kg, 7.5 mol, 1.0 equiv) dissolved in water (2.4 L, 2.0 rel. volumes) was added hydrazine dihydrochloride (870 g, 8.3 mol, 1.1 equiv). The mass was heated to 50-55° C. and stirred for 2 h, at which point HPLC showed 0.13% area remaining Compound 14. Subsequently, the reaction mass was cooled to 20-30° C. and basified to pH 9-11 using aqueous sodium carbonate (20%, w/w). Then the mixture was diluted with ethyl acetate (3.6 L, 3 rel. volumes) and filtered through Celite. The mixture was extracted with ethyl acetate (2×3.6 L, 2×3 rel. volumes), and the combined organic phases were concentrated in vacuo at 40° C. Yield: 1.17 kg (1.10 kg, 85%, adjust for EtOAc content).

Synthesis of Compound 16 To a mixture of the compound 15 residue (1.1 kg, 12.8 mol, 1.0 equiv) in MTBE (2.2 L, 2.0 rel. volumes) was added ethanolic-HCl (2.3 kg, 30% w/w, 1.5 equiv.) at 20-30° C. Subsequently, the reaction mixture was stirred at this temperature for 2 h before being cooled and stirred at 0-5° C. for 1 h. The resulting slurry was filtered, and the filter cake was washed with MTBE (1.1 L, 1.0 rel. volume) before being dried at 45-50° C. Yield: 1.2 kg (77%).

| $^1$H Data | $^{19}$F Data |
|---|---|
| 7.74 (d, 2H) | −181.64 |
| — | — |
| 12.93 (s, 2H) | — |

Synthesis of 4-fluoro-1H-pyrazole hydrochloride (Compound 16)

Synthesis B

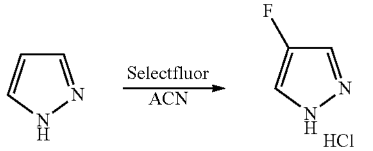

16

Selectfluor (0.25 eq) was added into a solution of 1H-pyrazole (1.0 eq, 20 g), in ACN (5 vol), and the mixture was stirred and heated to 80-85° C. for reaction and the SM limit was monitored (22% by area in HPLC). After completion of the reaction, the reaction mixture was cooled to RT and diluted with ethyl acetate (EA), filtered on a pad of wet silica gel, and finally washed the cake with EA. The filtrate was distilled to give crude and dissolved with EA. The organic layer was washed with HCl (1M) and distilled to get crude material. The crude solid was dissolved in EA and the organic layer was washed with 0.5M HCl, dried with $Na_2SO_4$ and evaporated. The mixture was redissolved in EA, and the organic layer was washed with 0.5HCl followed by brine. Finally the organic layer was dried over $Na_2SO_4$ and evaporated to give Compound 16 (F-pyrazole) which had purity 94.6% by HPLC with 3.4 g yield of the desired product.

Compound 16 (theoretical m/z 86.0280) was analyzed by mass spectrometry with electrospray ionization (ESI), in positive ion mode. ESI-MS showed the main measured mass (m/z) 87.03576 consistent with the Compound 16 form $[M+H]^+$ (m/z) 87.03530.

| $^1$H Data | $^{13}$C Data |
|---|---|
| 7.70 (d, $J_{H-F}$ = 4.5 Hz, 2H) | 120.18 (d, J = 21.0 Hz |
| — | 149.51 (d, J = 239.9 Hz) |
| 11.66 (s, 2H) | — |

Synthesis of 1-(6-Chloropyridin-3-yl)ethan-1-one (Compound 17) and 1-(6-(4-Fluoro-1H-pyrazol-1-yl)pyridin-3-yl)ethan-1-one (Compound 18)

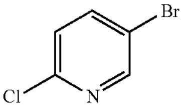

+

-continued

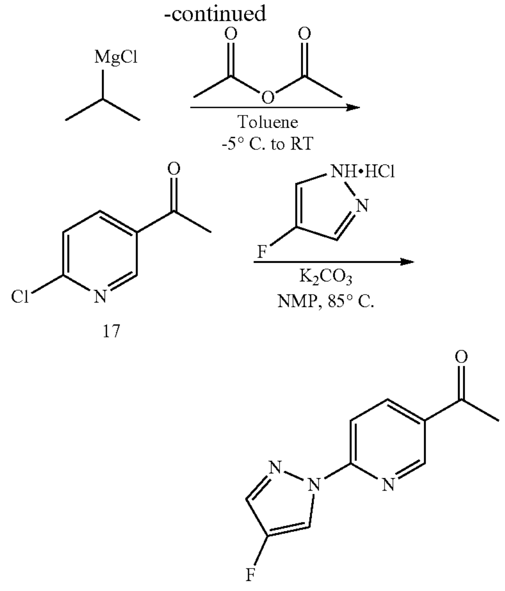

17

18

1-(6-Chloropyridin-3-yl)ethan-1-one Compound 17. To a solution of 5-bromo-2-chloropyridine (5.0 g, 1 eq, 26 mmol) in dry toluene (15 mL) at −5° C. was added isopropyl magnesium chloride (2 M, 18 mL, 1.4 eq, 36 mmol) over 45 min. The reaction mixture was stirred at RT overnight.

In a second flask, acetic anhydride (2.9 mL, 1.2 eq, 31 mmol) was diluted with dry toluene (15 mL) and the solution was cooled to −5° C. The Grignard solution was added over 15 min to the second flask while keeping the temperature between −5 and 0° C. The reaction was stirred at that temperature for 2 h.

The reaction was then quenched with 50 mL of saturated ammonium chloride solution in water and the phases were separated. The aqueous phase was extracted twice with 50 mL of toluene. The combined organic layers were washed with water and brine, dried over $Na_2SO_4$, and concentrated to afford 4.0 g of Compound 17 as a light-yellow solid.

The material was used in the next step without purification.

Compound 17 (theoretical monoisotopic mass 155.0138 amu) was analyzed by mass spectrometry with electrospray ionization (ESI), in positive ion mode. ESI-MS showed the main measured mass (m/z) 156.02106 consistent with the Compound 17 form $[M+H]^+$ with monoisotopic mass of 156.02107 amu.

| $^1H$ Data | $^{13}C$ Data |
|---|---|
| — | 196.28 |
| 2.62 (s, 3H) | 27.01 |
| — | 131.37 |
| 8.29 (dd, J = 8.3, 2.5 Hz, 1H) | 138.99 |
| 7.67 (dd, J = 8.3, 0.8 Hz, 1H) | 124.48 |
| — | 154.06 |
| 8.94 (dd, J = 2.5, 0.7 Hz, 1H) | 150.25 |

Synthesis of 1-(6-(4-Fluoro-1H-pyrazol-1-yl)pyridin-3-yl)ethan-1-one (Compound 18)

Compound 16 (4-Fluoro-1H-pyrazole hydrochloride, 500 mg, 1 eq, 4.0 mmol), Compound 17 (890 mg, 1.4 eq. 5.7 mmol) and potassium carbonate (1.18 g, 2.1 eq, 8.6 mmol) were dissolved with NMP (5 mL) in a 25 mL flask equipped with a condenser. The reaction mixture was stirred at 85° C. for 19 h. After reaction completion, the mixture was cooled down and 15 mL of water was added. The precipitate formed was filtered over a P4 filter and rinsed with 4 mL of water. The residue was dried under vacuum. To remove the minor impurities, the solid was dissolved in DCM and treated with charcoal. After stirring at RT for 30 min the solution was filtered over Celite and concentrated to afford Compound 18 as a light-brown solid in 86% yield and with good purity.

Compound 18 (theoretical m/z 205.0651) was analyzed by mass spectrometry with electrospray ionization (ESI) positive ion mode. Compound 18 was also analyzed by mass spectrometry with both electrospray ionization (ESI) and atmospheric pressure chemical ionization (APCI) techniques, both negative ion mode. ESI-MS positive ion mode showed a measured mass (m/z) 206.0724 consistent with the Compound 18 form $[M+H]^+$ (m/z) 206.0735. ESI-MS negative ion mode showed a measured mass (m/z) 206.0 consistent with the Compound 18 form $[M+H]^-$ (m/z) 206.0735.

| $^1H$ Data | $^{13}C$ Data |
|---|---|
| — | 195.98 |
| 2.64 (s, 3H) | 26.87 |
| — | 130.47 |
| 8.45 (dd, J = 8.6, 2.3 Hz, 1H) | 139.16 |
| 8.07-7.96 (m, 2H) | 111.02 (d, J = 1.6 Hz) |
| — | 152.78 |
| 9.01 (d, J = 2.3 Hz, 1H) | 149.36 |
| 8.77 (d, $J_{H-F}$ = 4.5 Hz, 1H) | 114.00 (d, J = 29.3 Hz) |
| — | 151.00 (d, J = 247.6 Hz) |
| 8.07-7.96 (m, 2H) | 131.59 (d, J = 15.1 Hz) |

Synthesis of (R)-N-((S)-1-(6-(4-fluoro-1H-pyrazol-1-yl)pyridin-3-yl)ethyl)-2-methylpropane-2-sulfinamide (Compound 20)

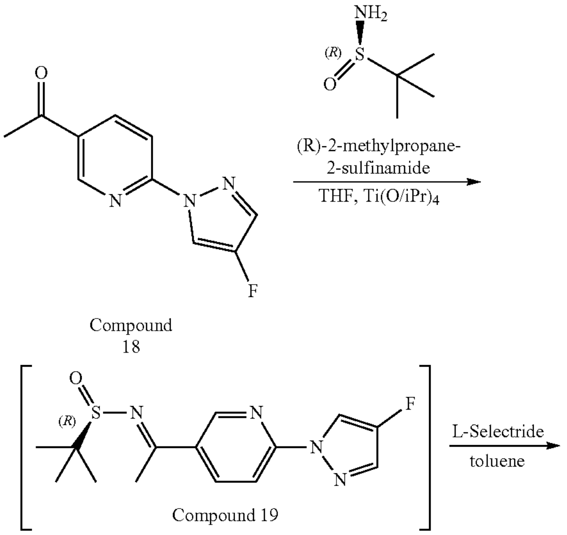

Compound 18

Compound 19

-continued

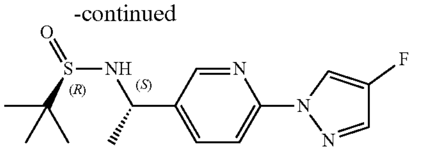

Compound 20

Compound 20 was prepared by reaction of Compound 18 (1.00 Kg 2% 1.0 eq.) with (R)-(+)-2-methyl-2-propane-2-sulfinamide (1.18 Kg±2%, 2.00 equivalents) in tetrahydrofuran (7.00 L±5%) in the presence of titanium (IV) isopropoxide (2.77 Kg±2%, 2.00 equivalents) at temperature between 70° C. and 80° C. to give Compound 19, non-isolated intermediate. The reaction mixture was cooled to a temperature between −15° C. and −25° C. and the L-Selectride solution (6.94 Kg±2%, 1.60 equivalents, toluene) was charged while maintaining the temperature to give Compound 20. N-Heptane may be added to the toluene to precipitate Compound 20 from solution.

Compound 20 (theoretical mass 310.1264 AMU) was analyzed by mass spectrometry with electrospray ionization (ESI), in positive ion mode. ESI-MS showed a measured mass (m/z) 311.1332 consistent with Compound 20 form [M+H]$^+$ (m/z) 311.1342.

| $^1$H Data | $^{13}$C Data |
|---|---|
| 5.54 (d, J = 5.4 Hz, 1H) | — |
| 4.52 (dq, J = 6.32, 6.32 Hz, 1H) | 52.24 |
| 1.51 (d, J = 6.7 Hz, 3H) | 24.20 |
| — | 138.67 |
| 7.96 (dd, J = 8.6, 2.3 Hz, 1H) | 137.86 |
| 7.93-7.83 (m, 2H) | 111.02 (d, J = 1.5 Hz) |
| — | 149.71 |
| 8.43 (d, J = 2.2 Hz, 1H) | 146.69 |
| 8.66 (dd, $J_{H-F}$ = 4.5 Hz, $J_{H-H}$ = 0.9 Hz, 1H) | 113.31 (d, J = 29.2 Hz) |
| — | 150.59 (d. J = 246.7 Hz) |
| 7.93-7.83 (m, 2H) | 129.90 (d, J = 14.7 Hz) |
| — | 55.09 |
| 1.10 (s, 9H) | 22.59 |

Synthesis of Compound 21

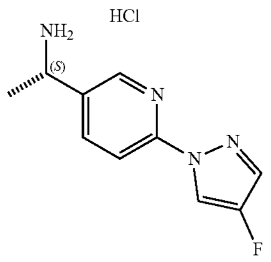

Compound 21 was prepared by the addition of Compound 20 (1.00 Kg±2%) portion-wise in not less than 1 hour in a solution of HCl (0.55 L±5%) in Acetone (8.00 L±5%) (alternatively, THF can be used instead of acetone) at a temperature between 15° C. and 25° C. A rinse with acetone (2.00 L±5%) was performed while maintaining the temperature between 15° C. and 25° C. The reaction was stirred until the content of Compound 20 relative to Compound 21 was lower than or equal to 1% area by UPLC. At the end of the reaction mixture was filtered and the reactor and solid were washed with acetone (2.00 L±5%) previously adjusted to a temperature between 15° C. and 25° C. The wet solid was dried under vacuum and nitrogen sweep at a temperature not more than 60° C. until the content of water by Karl Fischer was lower than, or equal to, 0.5% w/w and the content of Acetone was lower than 5000 ppm by GC. 85-100% yield. Compound 21 (theoretical m/z 206.0968, free amine) was analyzed by mass spectrometry with electrospray ionization (ESI), in positive ion mode. ESI-MS showed a measured mass (m/z) 207.1047 consistent with the compound 21 form [M+H]$^+$ (m/z) 207.1041.

| $^1$H Data | $^{13}$C Data |
|---|---|
| 8.75 (s, 3H) | — |
| 4.54 (q, J = 6.8 Hz, 1H) | 47.33 |
| 1.58 (d, J = 6.8 Hz, 3H) | 20.11 |
| — | 133.35 |
| 8.20 (dd, J = 8.6, 2.3 Hz, 1H) | 138.34 |
| 8.00-7.91 (m, 2H) | 111.14 (d, J = 1.5 Hz) |
| — | 150.55 |
| 8.63 (d, J = 2.3 Hz, 1H) | 147.51 |
| 8.72 (d, $J_{H-F}$ = 4.5 Hz, 1H) | 113.60 (d, J = 29.2 Hz) |
| — | 150.75 (d, J = 247.2 Hz) |
| 8.00-7.91 (m, 2H) | 130.46 (d, J = 14.8 Hz) |

Synthesis of Pralsetinib HCl Salt (Compound 22)

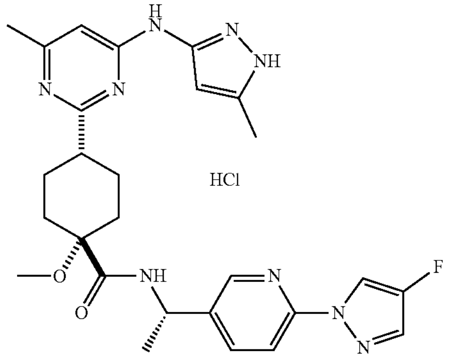

Compound 22 was prepared by adding a solution of Compound 21 (0.73 kg+2%, 1.1 eq) in deionized water (103835, 5.0 L±5%)/NMM (N-methyl morpholine) (1.5 L±2%) to a suspension previously prepared of Compound 9 (1.00 kg±2%, 1.0 eq)), CDMT (103593, 0.63 kg±2, 1.31 eq) in THF (100960, 5.0 L±5%)/deionized water (103835, 1.0 L±5%), during not more than 60 minutes and maintaining the temperature between 3° C. and 17° C. The reaction mixture was stirred at a temperature between 9° C. and 17° C. until the content of Compound 9 or Compound 21 was lower than, or equal to, 0.5% area by HPLC. When the reaction was complete, the mixture was cooled to 8-2° C. and quenched with HCl (1.2 L±5%), maintaining the temperature below 15° C. After adding about half the amount of HCl, the mixture crystallizes as agglomerates of needle-like particles. Absolute ethanol (6.0 L±5%) was then added and the resulting suspension was heated to reflux. The mixture was distilled at atmospheric pressure until a final volume of 21 L±5%, or 5 L±5% of the solvent was distilled. The jacket temperature used was normally less than 93° C. and the mixture temperature was usually between 74° C. and 81° C. The mixture was cooled to a temperature below 70° C.

Ethanol (5.0 L±5%) and isopropanol (6.0 L±5%) were charged. The suspension was heated to reflux temperature and stirred for 2 hours. The suspension obtained was cooled slowly to 25-20° C. The solid was isolated by filtration and washed twice with a mixture of absolute ethanol (1.0 L±5%), deionized water (1.0 L±5%), and isopropanol (1.0 L±5%). A wet solid sample was collected for IPC analysis by HPLC. The solid was dried under vacuum at a temperature lower than or equal to 50° C. until the water content by Karl-Fischer was lower than, or equal to, 3.0% w/w.

Further purification as needed.

The purification step consists in suspending the wet solid in isopropyl alcohol (6.0 L±5%), absolute ethanol (5.0 L±5%), and deionized water (5.0 L±5%). The suspension was heated to a temperature between 70° C. and 75° C., during 1 to 2 hours, and stirred for 1-3 hours at the same temperature range. Then, the suspension was cooled to a temperature between 38° C. and 42° C., during 1 to 2 hours. Heated to a temperature between 70° C. and 75° C., during 1 to 2 hours and stirred for 1-3 hours at the same temperature range. The resulting suspension was cooled to a temperature between 20° C. and 25° C. during 3.5 to 4.5 hours, and stirred for 1.5-3.5 hours at the same temperature range. The solid was isolated by filtration, washed twice with a mixture of ethanol (1.0 L±5%), isopropyl alcohol (1.0 L±5%), and deionized water (1.0 L±5%). A wet solid sample was collected for IPC analysis by HPLC The solid was dried under vacuum at a temperature lower than or equal to 50° C., until the water content by Karl-Fischer was lower than, or equal to, 3.0% w/w. A sample of the dry solid was collected for assay determination by HPLC.

The measured mass of (m/z) 534.2740 was consistent with the theoretical mass (m/z 534.2736) with the expected isotopic distribution for the $[MH]^+$ ion. Based on the high-resolution MS data, the calculated molecular formula was $C_{27}H_{33}FN_9O_2$ which was consistent with that of the pralsetinib protonated molecular ion.

| Pos. | $^1H$ Data | COSY | HSQC | HMBC | $^{13}C$ Data |
|---|---|---|---|---|---|
| 1 | 2.20 (s, 3H) | — | 1 | 2, 4, 5 | 10.71 |
| 2 | — | — | — | — | 138.16 |
| 3 | 11.89 (s. 1H) | — | — | 2, 4, 5 | — |
| 4 | — | — | — | — | 148.72 |
| 5 | 6.20 (s. 1H) | — | 5 | — | 95.32 |
| 6 | 9.51 (s, 1H) | — | — | — | — |
| 7 | — | — | — | — | 159.78 |
| 8 | 6.85 (s, 1H) | — | 8 | — | 101.65 |
| 9 | — | — | — | — | 164.33 |
| 10 | 2.23 (s. 3H) | — | 10 | 8, 9 | 23.82 |
| 11 | — | — | — | — | 172.02 |
| 12 | 2.57 (tt, J = 10.8, 5.2 Hz, 1H) | 13, 14 | 12 | 11, 13, 14 | 45.56 |
| 13, 14 | 1.77-1.67 (m, 2H); 1.88-1.77 (m. 2H) | 12, 15, 16 | 13, 14 | 11, 13-16 | 25.94, 25.98 |
| 15, 16 | 1.67-1.57 (m, 1H); 1.77-1.67 (m, 1H); 1.95-1.88 (m, 1H); 2.01-1.95 (m, 1H) | 13-16 | 15, 16 | 13-17, 19 | 30.03, 30.97 |
| 17 | — | — | — | — | 78.62 |
| 18 | 3.13 (s, 3H) | — | 18 | 17 | 50.81 |
| 19 | — | — | — | — | 173.47 |
| 20 | 8.47 (d, J = 8.3 Hz, 1H) | 21 | — | 19, 21, 22 | — |
| 21 | 5.05 (dq, J = 7.2 Hz, 1H) | 20, 22 | 21 | 19, 22, 23, 24, 27 | 45.41 |
| 22 | 1.46 (d, J = 7.1 Hz, 3H) | 21 | 22 | 21, 23 | 21.58 |
| 23 | — | — | — | — | 138.88 |
| 24 | 7.99 (dd, J = 8.5, 2.3 Hz, 1H) | 25, 27 | 24 | 21, 26, 27 | 137.36 |
| 25 | 7.87 (dd, J = 8.4, 0.8 Hz, 1H) | 24 | 25 | 23, 26 | 111.04 (d, $J_{C-F}$ = 1.5 Hz) |
| 26 | — | — | — | — | 149.49 |
| 27 | 8.43 (d, J = 2.3 Hz, 1H) | 24 | 27 | 21, 23-26 | 146.19 |
| 28 | 8.67 (dd, $J_{H-F}$ = 4.6 & $J_{H-H}$ = 0.9 Hz, 1H) | 30 | 28 | 29, 30 | 113.35 (d, $J_{C-F}$ = 29.2 Hz) |
| 29 | — | — | — | — | 150.59 (d, $J_{C-F}$ = 246.7 Hz) |
| 30 | 7.90 (dd, $J_{H-F}$ = 4.3 & $J_{H-H}$ = 0.9 Hz, 1H) | 28 | 30 | 28, 29 | 129.85 (d, $J_{C-F}$ = 14.6 Hz) |

Synthesis of Pralsetinib (Compound 23)

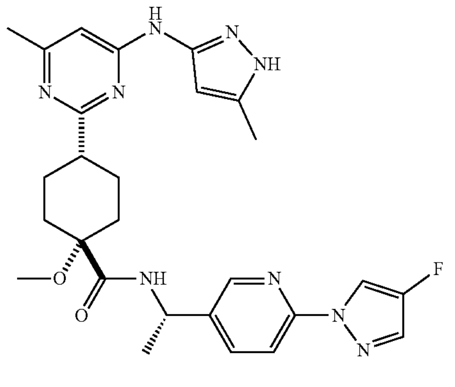

Pralsetinib was prepared by charging sodium hydroxide solution, previously prepare with deionized water (5.0 L±5%, 5.0 Kg±5%) and sodium hydroxide (50% w/w) (0.55 L±5%, 0.84 Kg±5%), to a suspension of Compound 22 (1.00 Kg±2%-assay basis) in dichloromethane (12.0 L±5%□15.94 Kg±5%), in not less than 15 minutes. The charging system was rinsed with deionized water (1.0 L±5% 1.0 Kg±5%) and the rinse was charged to the main solution.

The mixture was heated to a temperature between 35° C. and 45° C. and stir at this temperature during not less than 2 hours. The pH of the mixture was verified. If the pH was lower than 12, more sodium hydroxide solution was charged, in the same concentration as prepared previously, until the pH is met. It was confirmed if a clear biphasic mixture was obtained. If solids were present in the mixture, the mixture should be stirred for not less than 2 hours at a temperature between 35° C. and 45° C. The phases were separated for not less than 30 minutes. The organic phase 1 (bottom phase) obtained (lower phase, containing the product) was stored. The aqueous phase 1 (upper phase) was kept in the same reactor. If solids were present, the solids were maintained in the aqueous phase. Dichloromethane (5.0 L±5% 6.64 Kg±5%) was charged to aqueous phase 1 and stirred for not less than 30 minutes, maintaining the temperature between 25° C. and 35° C. The phases were allowed to separate for not less than 30 minutes. The organic phase obtained (organic phase 2, lower phase) was combined with the previous organic phase (organic phase 1) and if solids were present were maintained with the organic phase. The aqueous phase 2 (upper phase) was discarded. Deionized water (6.0 L±5% 6.0 Kg±5%) was charged to the combined organic phase, maintaining the temperature between 25° C. and 35° C., and then, stirred for not less than 30 minutes. The phases were allowed to separate for not less than 30 minutes. The rag layer was maintained with organic phase 3 (lower phase) and the aqueous phase 3 (upper phase) was discharged. The organic phase 3 was washed again with deionized water (103835; 6.0 L±5% 6.0 Kg±5%) and stirred for not less than 30 minutes. The phases were allowed to separate for not less than 30 minutes. The organic phase 4 obtained (lower phase) was transfer to a reactor for distillation. The organic phase 4 was distilled at atmospheric pressure until a final volume of 4.0 L±5%. It was expected that the distillation occurs at a temperature between 38° C. and 40° C. Acetone (9.0 L±5% 7.1 Kg±5%) and deionized water (1.0 L±5% 1.0 Kg±5%) were charged and the mixture is distilled at atmospheric pressure until a final volume of 8.0 L±5%. The distillation occurred at a temperature between 51° C. and 57° C. Acetone (9.0 L±5% 7.1 Kg±5%) and deionized water (1.0 L±5% 1.0 Kg±5%) were charged again and the mixture is distilled again at atmospheric pressure until a final volume of 8.0 L±5%. This distillation occurred at a temperature between 51° C. and 60° C. Acetone (9.0 L±5% 7.1 Kg±5%) and deionized water (1.0 L±5% 1.0 Kg±5%) were charged one more time. The temperature was adjusted between 40° C. and 30° C. and the mixture was filtered, through a filter with porosity less than 1 micron. The previous reactor and transfer lines were rinsed with a mixture of acetone (3.0 L±5% 2.4 Kg±5%) and deionized water (0.2 L±5% 0.2 Kg±5%) The mixture was distilled at atmospheric pressure until a final volume of 8.0 L±5%. This distillation occurred at a temperature between 52° C. and 62° C. The mixture was cooled to a temperature between 50° C. and 55° C. A sample was taken for water content determination by Karl-Fisher. The water content value, determined by Karl-Fischer volumetric titration as % w/w (using one decimal place), was used to calculate the deionized water and acetone to be charged.

Calculation of Acetone Charge=6.32×[KF % (w/w)/100]=*XX* Kg

Calculation of Deionized water Charge=3.50−[8×[KF % (w/w])/100]]=*YY* Kg

Note: According to the equation, for values of water content above 43.7% (w/w) by Karl-Fisher no water should be added.

After adjusting the acetone and water, the mixture was cooled to a temperature between 35° C. and 45° C. preferentially 5° C./h, and then seeded with (0.005 Kg±5%) or Compound 23 (0.005 Kg±5%) and then the charging system was rinsed with a mixture of deionized water (0.06 Kg±5% 0.06 L±5%) and acetone (0.011 Kg±5% 0.014 L±5%), Adjust temperature between 40 and 45° C. and stirred during not less than 30 minutes, at the same temperature range. The seed can also be charged directly to the mixture and the mixture of deionized water and acetone can be used to rinse the charging system. Deionized water (10.5 L±5% 10.5 Kg±5%), is added over 3 to 5 hours, maintaining the temperature between 40° C. and 45° C. The resulting suspension was heated to reflux temperature, over 2 to 3 hours, and stir 2 to 3 hours at reflux temperature. The reflux temperature was expected at about 68° C. The suspension was cooled to a temperature between 25° C. and 15° C., over 5 to 6 hours, and stirred at the same temperature range for 5 to 6 hours. The solid was isolated by filtration, washed with a mixture of acetone (0.7 L±5% 0.6 Kg±5%) and deionized water (1.3 L±5% 1.3 Kg±5%), previously filtered through a filter with porosity less than 1 micron. The solid was dried under vacuum at a temperature lower than or equal to 50° C. until the content of water by Karl-Fischer was lower or equal to 4.0% (w/w).~97% yield.

The measured mass of (m/z) 534.2740 was consistent with the theoretical mass (m/z 534.2736) with the expected isotopic distribution for the $[MH]^+$ ion. Based on the high-resolution MS data, the calculated molecular formula was $C_{27}H_{33}FN_9O_2$ which was consistent with that of the pralsetinib protonated molecular ion.

| Pos. | $^1H$ Data | COSY | HSQC | HMBC | $^{13}C$ Data |
|---|---|---|---|---|---|
| 1 | 2.20 (s, 3H) | — | 1 | 2, 4, 5 | 10.71 |
| 2 | — | — | — | — | 138.16 |
| 3 | 11.89 (s, 1H) | — | — | 2, 4, 5 | — |
| 4 | — | — | — | — | 148.72 |
| 5 | 6.20 (s, 1H) | — | 5 | — | 95.32 |
| 6 | 9.51 (s, 1H) | — | — | — | — |
| 7 | — | — | — | — | 159.78 |
| 8 | 6.85 (s. 1H) | — | 8 | — | 101.65 |
| 9 | — | — | — | — | 164.33 |
| 10 | 2.23 (s, 3H) | — | 10 | 8, 9 | 23.82 |
| 11 | — | — | — | — | 172.02 |
| 12 | 2.57 (tt, J = 10.8, 5.2 Hz, 1H) | 13, 14 | 12 | 11, 13, 14 | 45.56 |
| 13, 14 | 1.77-1.67 (m, 2H); 1.88-1.77 (m, 2H) | 12, 15, 16 | 13, 14 | 11, 13-16 | 25.94, 25.98 |

-continued

| Pos. | $^{1}$H Data | COSY | HSQC | HMBC | $^{13}$C Data |
|---|---|---|---|---|---|
| 15, 16 | 1.67-1.57 (m, 1H); 1.77-1.67 (m, 1H); 1.95-1.88 (m, 1H); 2.01-1.95 (m, 1H) | 13-16 | 15, 16 | 13-17, 19 | 30.03, 30.97 |
| 17 | — | — | — | — | 78.62 |
| 18 | 3.13 (s, 3H) | — | 18 | 17 | 50.81 |
| 19 | — | — | — | — | 173.47 |
| 20 | 8.47 (d, J = 8.3 Hz, 1H) | 21 | — | 19, 21, 22 | — |
| 21 | 5.05 (dq, J = 7.2 Hz, 1H) | 20, 22 | 21 | 19, 22, 23, 24, 27 | 45.41 |
| 22 | 1.46 (d, J = 7.1 Hz, 3H) | 21 | 22 | 21, 23 | 21.58 |
| 23 | — | — | — | — | 138.88 |
| 24 | 7.99 (dd, J = 8.5, 2.3 Hz, 1H) | 25, 27 | 24 | 21, 26, 27 | 137.36 |
| 25 | 7.87 (dd, J = 8.4, 0.8 Hz, 1H) | 24 | 25 | 23, 26 | 111.04 (d, $J_{C-F}$ = 1.5 Hz) |
| 26 | — | — | — | — | 149.49 |
| 27 | 8.43 (d, J = 2.3 Hz, 1H) | 24 | 27 | 21, 23-26 | 146.19 |
| 28 | 8.67 (dd, $J_{H-F}$ = 4.6 & $J_{H-H}$ = 0.9 Hz, 1H) | 30 | 28 | 29, 30 | 113.35 (d, $J_{C-F}$ = 29.2 Hz) |
| 29 | — | — | — | — | 150.59 (d, $J_{C-F}$ = 246.7 Hz) |
| 30 | 7.90 (dd, $J_{H-F}$ = 4.3 & $J_{H-H}$ = 0.9 Hz, 1H) | 28 | 30 | 28, 29 | 129.85 (d, $J_{C-F}$ = 14.6 Hz) |

The invention claimed is:

1. A compound selected from the group consisting of:

a compound of Formula (I):

(I)

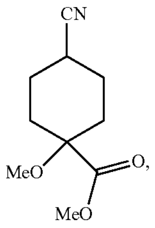

or a salt thereof;

a compound of Formula (II):

(II)

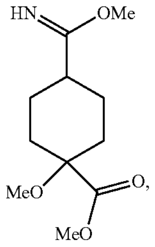

or a salt thereof; and a compound of Formula (III):

(III)

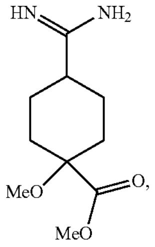

or a salt thereof.

2. The compound of claim 1, wherein the compound is a compound of Formula (Ia):

(Ia)

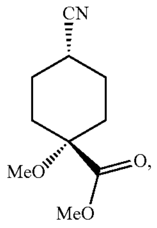

or a salt thereof.

3. The compound of claim 1, wherein the compound is a compound of Formula (Ib):

(Ib)

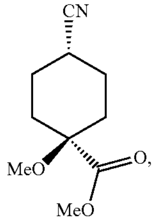

or a salt thereof.

4. The compound of claim 1, wherein the compound is a compound of Formula (IIa):

(IIa)

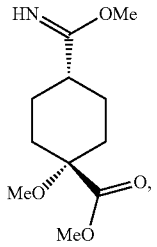

or a salt thereof.

5. The compound of claim 1, wherein the compound is a compound of Formula (IIb):

(IIb)

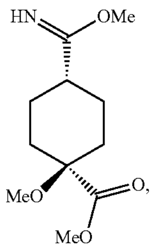

or a salt thereof.

6. The compound of claim 1, wherein the compound is a compound of Formula (IIIa):

(IIIa)

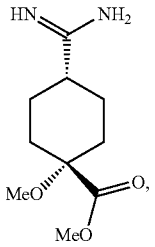

or a salt thereof.

7. The compound of claim 1, wherein the compound is a compound of Formula (IIIb):

(IIIb)

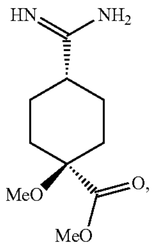

or a salt thereof.

8. A compound of Formula V:

(V)

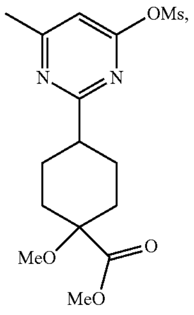

or a salt thereof.

9. The compound of claim 8, wherein the compound is a compound of Formula (Va):

(Va)

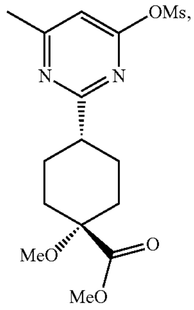

or a salt thereof.

10. The compound of claim 8, wherein the compound is a compound of Formula (Vb):

(Vb)

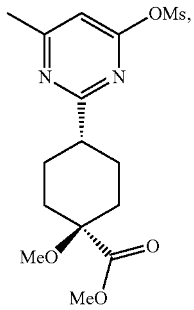

or a salt thereof.

11. A composition comprising a compound of Formula VI:

(VI)

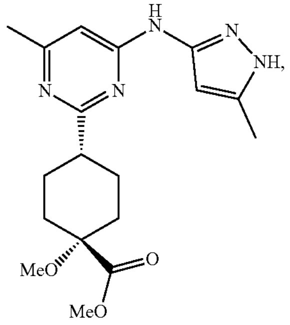

or a salt thereof, wherein the composition comprises the compound of Formula (VI) or a salt thereof and the compound of Formula (VIa) or a salt thereof in a ratio of greater than or equal to about 9:1:

(VIa)

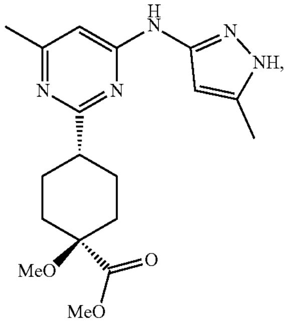

or a salt thereof.

12. The composition of claim 11, wherein the ratio of the compound of Formula (VI) or a salt thereof and the compound of Formula (VIa) or a salt thereof is greater than or equal to about 97 to 3.

13. The composition of claim 11, wherein the ratio of the compound of Formula (VI) or a salt thereof and the compound of Formula (VIa) or a salt thereof is detected using HPLC.

14. A composition comprising a compound of Formula (VII):

(VII)

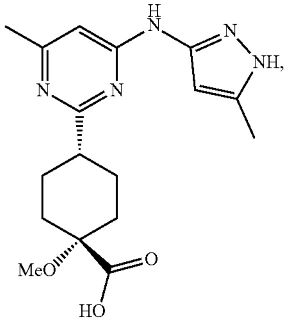

or a salt thereof, wherein the composition comprises the compound of Formula (VII) or a salt thereof and the compound of Formula (VIIa) or a salt thereof in a ratio of greater than or equal to about 9:1:

(VIIa)

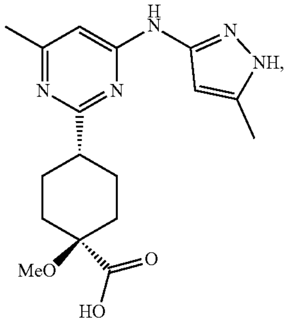

or a salt thereof.

15. The composition of claim 14, wherein the ratio of the compound of Formula (VII) or a salt thereof and the compound of Formula (VIIa) or a salt thereof is greater than or equal to about 97 to 3.

16. A process of preparing a composition comprising a mixture of cis and trans isomers of a compound of Formula (IV):

(IV)

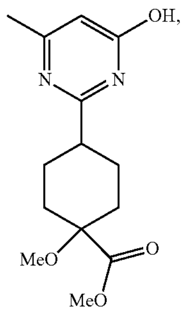

or a salt thereof, wherein the process comprises:

(a) reacting a compound of Formula (II):

(II)

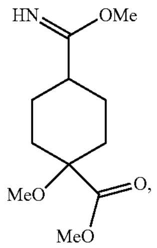

or a salt thereof with an ammonium source in the presence of a solvent, thereby producing a compound of Formula (III):

(III)

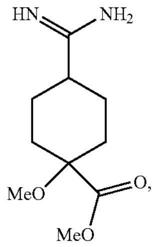

or a salt thereof; and (b) reacting a compound of Formula (III) with alkyl acetoacetate, thereby producing a composition comprising a mixture of cis and trans isomers of a compound of Formula (IV) having a greater amount of the cis isomer, Formula (IVa):

(IVa)

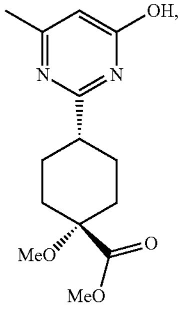

or a salt thereof, as compared to the trans isomer, Formula (IVb):

(IVb)

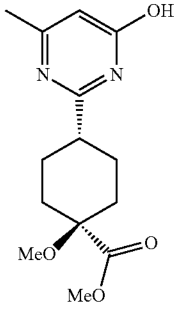

or a salt thereof.

17. A process of preparing a compound of Formula (X):

(X)

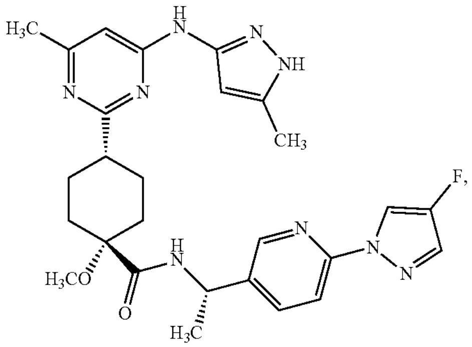

or a salt thereof, comprising the steps of:

(a) reacting a compound of Formula (II):

(II)

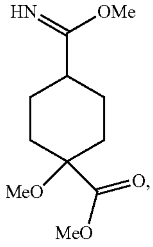

or a salt thereof with an ammonium source in the presence of a solvent, thereby producing a compound of Formula (III):

(III)

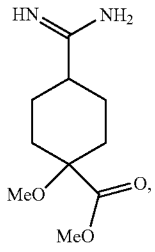

or a salt thereof;

(b) reacting a compound of Formula (III) with alkyl acetoacetate, thereby producing an isomeric mixture of a compound of Formula (IV):

(IV)

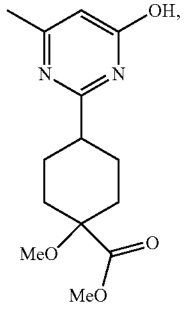

or a salt thereof, wherein the isomeric mixture of the compound of Formula (IV) has a greater amount of the cis isomer, Formula (IVa):

(IVa)

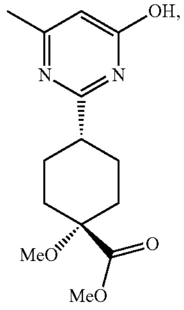

or a salt thereof, as compared to the trans isomer, Formula (IVb):

(IVb)

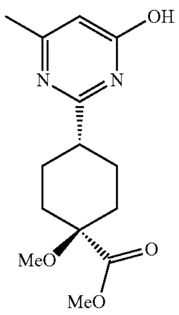

or a salt thereof;

(c) purifying the isomeric mixture of the compound of Formula (IV) or a salt thereof to obtain the compound of Formula (IVa) or a salt thereof;

(d) reacting the compound of Formula (IVa) or a salt thereof with an activating agent, thereby providing a compound of Formula (V-1a):

(V-1a)

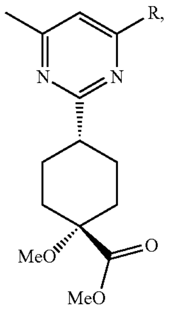

or a salt thereof, wherein R is an activating group;

(e) reacting the compound of Formula (V-la) or a salt thereof with 5-methyl-3-pyrazolamine, thereby providing a compound of Formula (VI):

(VI)

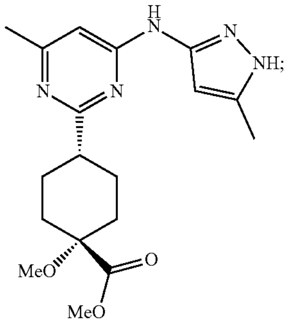

or a salt thereof;

(f) reacting the compound of Formula (VI) or a salt thereof with a base, thereby providing a compound of Formula (VII):

(VII)

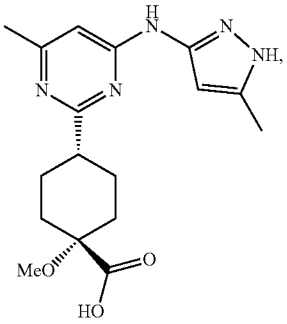

or a salt thereof;

(g) reacting the compound of Formula (VII) or a salt thereof with a compound of Formula (VIII):

(VIII)

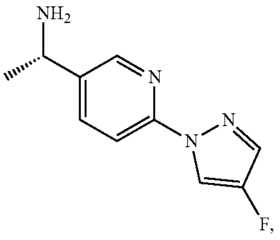

or a salt thereof, thereby providing the compound of Formula (X) or a salt thereof.

18. The process of claim 17, wherein the last step of the process further comprises reacting a salt of a compound of Formula (X) with a base, thereby providing a compound of Formula (X).

19. The process of claim 18, wherein the salt of a compound of Formula (X) is an HCl salt.

20. An isomeric mixture of cis and trans isomers of a compound of Formula (IV):

(IV)
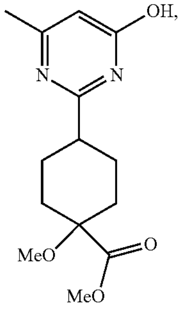
or a salt thereof, wherein the cis isomer is a compound of Formula (IVa):
(IVa)
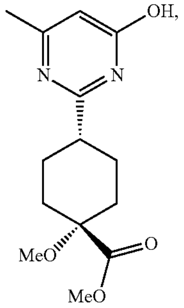
and the trans isomer is a compound of Formula (IVb):
(IVb)
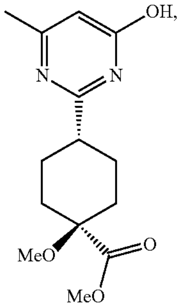
or a salt thereof, wherein the ratio of the cis isomer to the trans isomer is greater than or equal to about 5:1.
* * * * *